(12) United States Patent
Chuang et al.

(10) Patent No.: US 7,924,892 B2
(45) Date of Patent: Apr. 12, 2011

(54) FIBER AMPLIFIER BASED LIGHT SOURCE FOR SEMICONDUCTOR INSPECTION

(75) Inventors: Yung-Ho Chuang, Cupertino, CA (US); J. Joseph Armstrong, Milpitas, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 11/056,855

(22) Filed: Feb. 11, 2005

(65) Prior Publication Data

US 2006/0045163 A1  Mar. 2, 2006

Related U.S. Application Data

(60) Provisional application No. 60/604,540, filed on Aug. 25, 2004, provisional application No. 60/620,814, filed on Oct. 20, 2004.

(51) Int. Cl.
*H01S 3/30* (2006.01)

(52) U.S. Cl. .................. 372/6; 372/10; 372/17; 372/18

(58) Field of Classification Search ................ 372/6, 10, 372/17
See application file for complete search history.

(56) References Cited

U.S. PATENT DOCUMENTS

| | | | |
|---|---|---|---|
| 3,646,462 A | 2/1972 | Snitzer | |
| 5,023,845 A | 6/1991 | Crane et al. | |
| 6,014,249 A | 1/2000 | Fermann et al. | |
| 6,208,458 B1 * | 3/2001 | Galvanauskas et al. | 359/345 |
| 6,317,443 B1 * | 11/2001 | Craig et al. | 372/38.04 |
| 7,054,339 B1 * | 5/2006 | Hu et al. | 372/12 |
| 2002/0054613 A1 * | 5/2002 | Kang | 372/6 |
| 2002/0122644 A1 * | 9/2002 | Birks et al. | 385/125 |
| 2002/0131162 A1 * | 9/2002 | Beeson | 359/342 |
| 2002/0168161 A1 * | 11/2002 | Price et al. | 385/123 |
| 2003/0008448 A1 | 1/2003 | Kafka et al. | |
| 2004/0057682 A1 * | 3/2004 | Nicholson et al. | 385/122 |
| 2005/0169326 A1 * | 8/2005 | Jacob et al. | 372/22 |
| 2005/0213710 A1 * | 9/2005 | Lawrence et al. | 378/121 |
| 2005/0232313 A1 * | 10/2005 | Fermann et al. | 372/6 |
| 2005/0259314 A1 * | 11/2005 | Tokuhisa et al. | 359/326 |
| 2008/0232407 A1 * | 9/2008 | Harter et al. | 372/6 |
| 2009/0060438 A1 * | 3/2009 | Mori et al. | 385/127 |
| 2009/0122815 A1 * | 5/2009 | Jiang et al. | 372/18 |

FOREIGN PATENT DOCUMENTS

JP   2003008115   1/2003

\* cited by examiner

*Primary Examiner* — Dung T Nguyen

(74) *Attorney, Agent, or Firm* — Smyrski Law Group, A P.C.

(57) ABSTRACT

A laser illuminator for use in an inspection system, such as a semiconductor wafer inspection system or photomask inspection system is provided. The gain medium in the illuminator comprises optical fiber, and amplification, beam splitting, frequency and/or bandwidth conversion, peak power reduction, and q-switching or mode locking may be employed. Certain constructs including doped fiber, gratings, saturable absorbers, and laser diodes are disclosed to provide enhanced illumination.

27 Claims, 24 Drawing Sheets

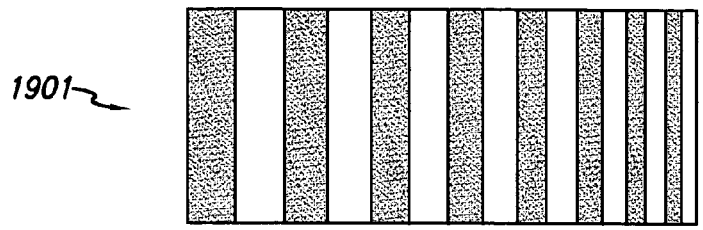
FIG. 19
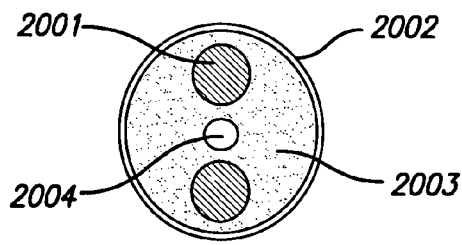
FIG. 20
FIG. 21
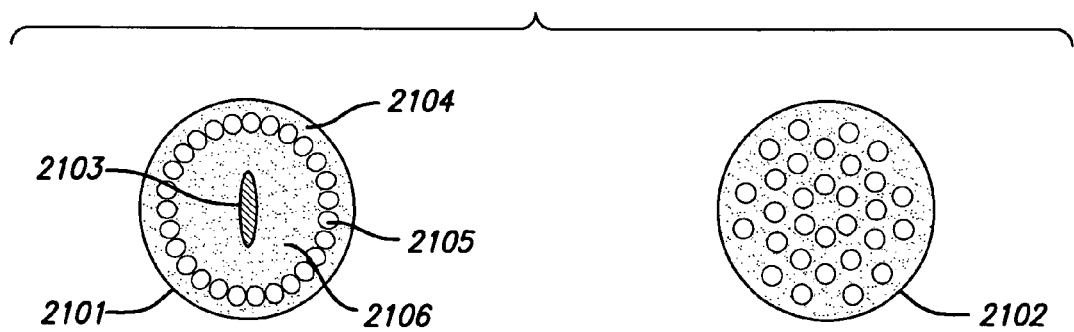

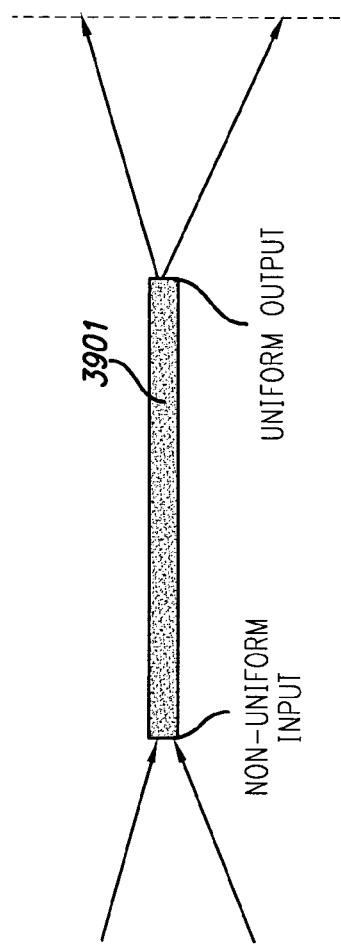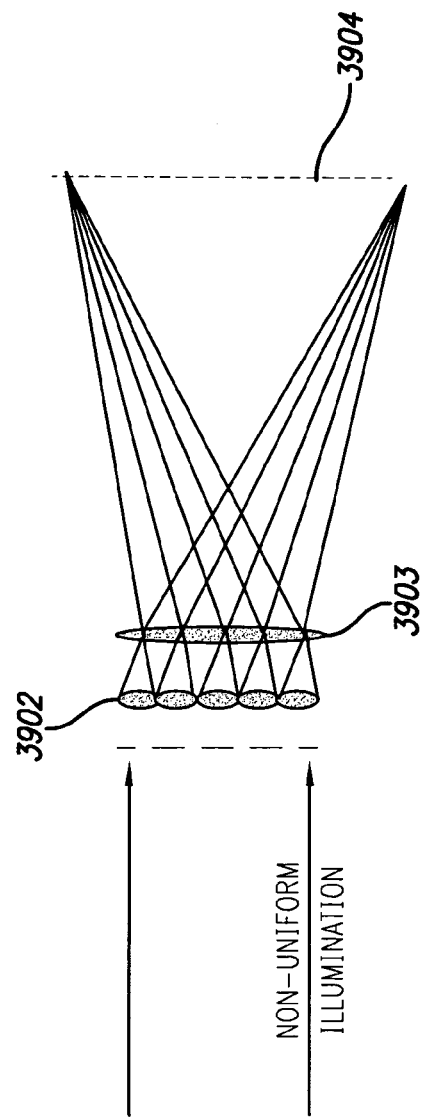
FIG. 39A
FIG. 39B

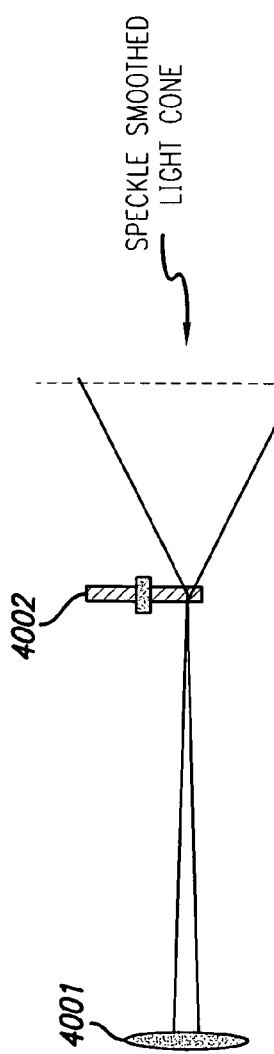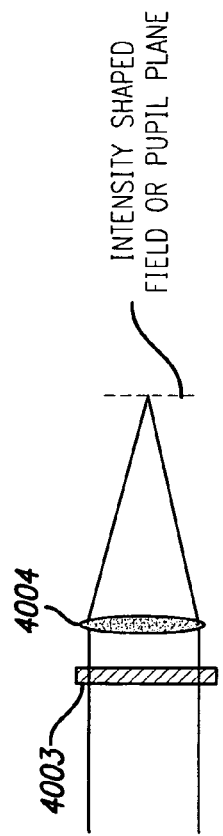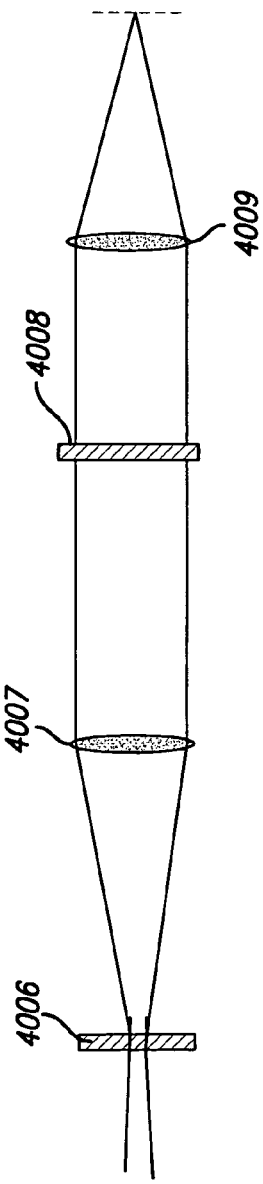

FIBER AMPLIFIER BASED LIGHT SOURCE FOR SEMICONDUCTOR INSPECTION

This application claims the benefit of U.S. Provisional Patent Application Ser. No. 60/604,540, entitled "Fiber Amplifier Based Light Source for Semiconductor Inspection," filed Aug. 25, 2004, and U.S. Provisional Patent Application Ser. No. 60/620,814, entitled "Coherent DUV Sources for Semiconductor Wafer Inspection," filed Oct. 20, 2004.

BACKGROUND OF THE INVENTION

1. Field of the Invention

The present invention generally relates to illuminators used in conjunction with inspection systems, such as semiconductor wafer inspection systems and photomask inspection systems, and more particularly to a fiber amplifier based light source for use with such inspection systems.

2. Description of the Related Art

The demands of the semiconductor industry for wafer and photomask inspection systems exhibiting high throughput and improvements in resolution are ongoing. Successive generations of such inspection systems tend to achieve higher resolution by illuminating the wafer or reticle using light energy having shorter wavelengths.

Certain practical advantages may be achieved when illuminating the wafer or reticle with light of multiple wavelengths including UV-DUV wavelengths. Providing suitable lasers for high quality wafer and photomask inspection systems presents a particular challenge. Conventional lasers generating multiple wavelengths or relatively short wavelength light energy are typically large, expensive devices with relatively short lifetimes and low average power. Wafer and photomask inspection systems generally require a laser generally having a high average power, low peak power, and relatively short wavelength for sufficient throughput and an adequate defect signal-to-noise ratio (SNR).

Of the currently available lasers, excimer lasers are a source of short wavelength, high average power light. However, excimer lasers tend to operate at a slow repetition rate, such as in the range of 4 to 10 kHz. Repetition rates in this range tend to create extremely high peak power levels and can damage the wafer or reticle. Excimer lasers therefore cannot meet requirements for many precision wafer and reticle inspection systems.

Another option to provide adequate DUV power entails generating shorter wavelength light from a longer wavelength source. This wavelength alteration process is commonly called frequency conversion. Frequency conversion can be inefficient, and can require a high peak power laser to provide sufficient light to the frequency conversion crystal.

Using frequency conversion, a system generating adequate short wavelength power needs to generate sufficient long wavelength power. Generating sufficient long wavelength power can be challenging or impossible with a conventional laser. One method for increasing the amount of long wavelength power entails adding an amplifier to the original laser source. Laser amplifiers present certain issues including generally poor spatial profiles, nonlinear effects, and can experience an effect known as thermal lensing. Thermal lensing occurs when the refractive index of the gain medium varies with temperature, and the temperature of the gain medium always varies with the intensity of the light propagating through the amplifier. Controlling this variation in a high power laser with sufficient precision is difficult, if not impossible. When the temperature of the laser changes, the spatial profile of the beam tends to change. A non-Gaussian beam tends to degrade the frequency conversion process and can damage optical components.

In this environment, a laser based illuminator or illuminating arrangement having multiple wavelengths that include ultraviolet-deep ultraviolet (UV-DUV) wavelengths may provide benefits over previous types of illuminators. Such an illuminating arrangement operating at sufficient power levels to provide adequate SNRs that are relatively inexpensive, have relatively long lifetimes may be preferable to other illuminators depending on the application.

It would be beneficial to provide a system overcoming these drawbacks present in previously known systems and provide an optical inspection system illumination design having improved functionality over devices exhibiting those negative aspects described herein.

SUMMARY OF THE INVENTION

According to one aspect of the present design, there is provided an illuminator employed in a specimen inspection system. The illuminator comprises at least one optical fiber configured to receive light energy and transmit the light energy toward the specimen. The illuminator may include at least one fiber laser amplifier, and performance of the illuminator may be enhanced or operated in various scenarios using a variety of additional hardware or using different methodologies.

These and other advantages of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which:

FIG. 19 is a chirped grating;

FIG. 20 shows one type of polarization-preserving fiber having a solid core;

FIG. 21 illustrates two cross sections of polarization-preserving photonic crystal fiber;

FIG. 39A illustrates a first spatial smoothing media;

FIG. 39B shows a second spatial smoothing media;

FIG. 40A shows a first additional example of spatial smoothing media;

FIG. 40B shows a second additional example of spatial smoothing media;

FIG. 40C shows a third additional example of spatial smoothing media;

DETAILED DESCRIPTION OF THE INVENTION

According to the present design, a fiber amplifier based light source for semiconductor inspection can be achieved wherein the gain medium consists of optical fiber. Alternately, an illuminator for a wafer inspection system or photomask inspection system is provided comprising at least one laser oscillator and at least one fiber laser amplifier. The laser oscillator may be a solid-state laser or semiconductor diode laser, and the laser oscillator may incorporate means for creating a q-switched or mode-locked pulse train. Various devices may be employed to enhance performance of the illuminator, including but not limited to peak power reducing hardware, frequency conversion media, spatial shifting media, spatial smoothing media, image relay hardware, and temporal shifting media.

Figure 1:
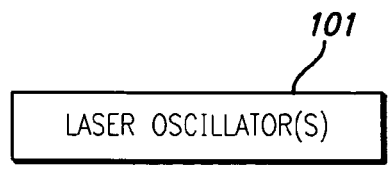
FIG. 1 illustrates a laser oscillator.
Figure 2:
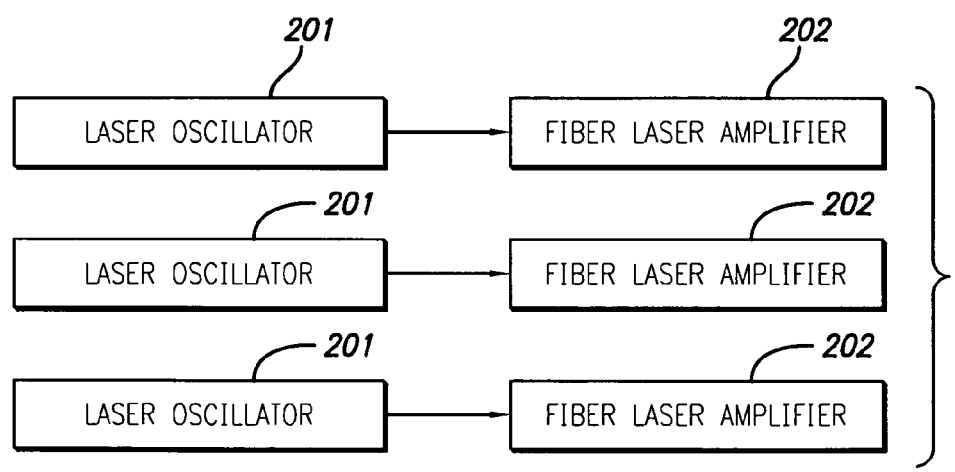
FIG. 2 shows an illuminator combining one or more laser oscillators with one or more fiber laser amplifiers.

FIGS. 1 and 2 illustrate an illuminator for a wafer or photomask inspection system. FIG. 1 shows a laser oscillator 101, while FIG. 2 shows a slightly more complex illuminator combining one or more laser oscillators 201 with one or more fiber laser amplifiers 202. The present design is an illuminator for a wafer inspection system or a photomask inspection system wherein the gain media comprises optical fiber. Optical fiber technology, with the addition of optical crystals, allows for tuning light wavelengths by broadening narrowband light or shifting light from one narrowband wavelength to another.

The present design also addresses illuminating a wafer or photomask for inspection, including using one or more lasers to generate coherent light, and subsequently amplifying the coherent light with one or more fiber laser amplifiers. In certain embodiments, the design may also maintain single mode propagation within the fiber laser amplifier as discussed below.

Figure 3:
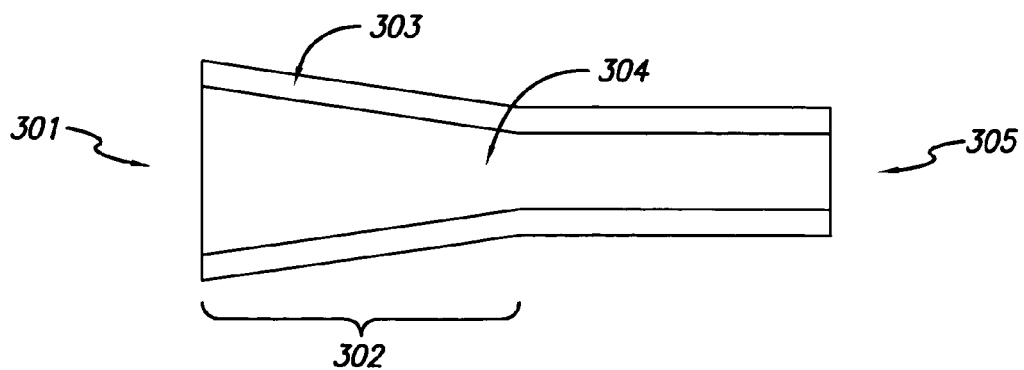
FIG. 3 is a large diameter fiber having a tapered end.

Power-handling capability of the fiber laser amplifier 202 may be enhanced by employing a fiber with a relatively large diameter, but this can diminish wavefront quality and the fiber laser amplifier 202 may exhibit multi-mode behavior. In the present design, the fiber laser amplifier 202 may comprise a large diameter fiber having a tapered end as shown in FIG. 3. The photons enter the tapered area through the large area input 301. The size of the core 304 decreases in the tapered region 302, while the size of the cladding 303 may decrease or remain constant. The tapered end tends to suppress higher order modes in a fiber laser amplifier. The beam exits the fiber and propagates in a single mode to and through output 305.

Figure 4:
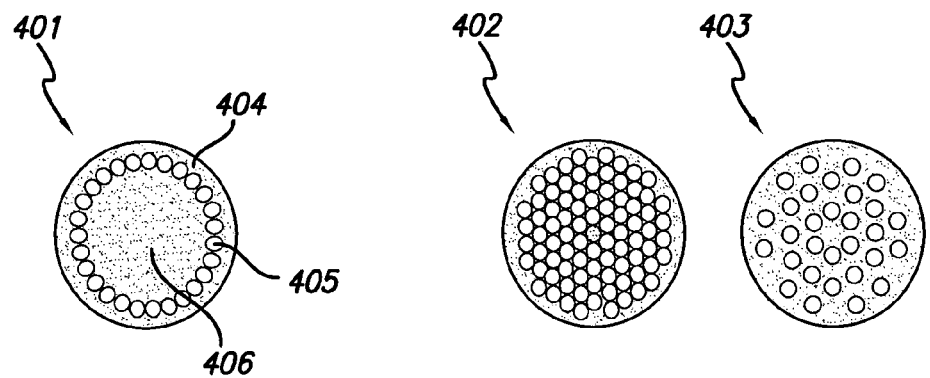
FIG. 4 shows three examples of cross sections of photonic crystal fiber.

An alternate design provides a high quality wavefront with a single mode (i.e., a Gaussian beam profile) by incorporating a photonic crystal fiber into the fiber laser amplifier 202 or an optical fiber with a modified index profile. The photonic crystal fiber may be a multi-core fiber. FIG. 4 shows three examples of cross sections of photonic crystal fiber 401, 402, and 403. In all three examples, the gray regions represent either glass or doped glass and the white regions represent air. The first fiber 401 shows a doped fiber core 406, external cladding 404, and multiple channels of air cladding 405 arranged in a ring configuration. The second fiber 402 and third fiber 403 illustrate air cladding channels arranged in a honeycomb configuration. These configurations are generally spatially uniform along the fiber length. Air cladding channels 405 facilitate a high-quality wavefront having a single mode within a fiber having a diameter greater than approximately 50 microns.

The mode area may be increased, where the mode area is the area taken up by the fiber optic media, and a single mode output obtained within the fiber laser amplifier 202 by bending the fiber laser amplifier, by tapering the end of the fiber laser amplifier, or by modifying the refractive index of the fiber laser amplifier 202.

Within the bandwidth of the laser oscillator 201, the frequency for amplifying the fiber laser amplifier 202 may be assessed by doping the fiber laser amplifier 202 with an appropriate lanthanide element such as ytterbium, erbium, thulium, neodymium, praseodymium, or holmium.

Nonlinear effects can broaden the narrowband light which leaves the fiber laser amplifier and are generally undesirable. Broadband light can diminish the efficiency of the subsequent frequency conversion process. In the present design, nonlinear effects are addressed by either expanding the light energy pulse (in time) before the pulse enters the fiber laser amplifier 202, or using a fiber that can produce a relatively large single mode output. Relatively large single mode outputs can be achieved by incorporating a hybrid photonic crystal fiber with pump cladding into the fiber laser amplifier 202.

Figure 5:
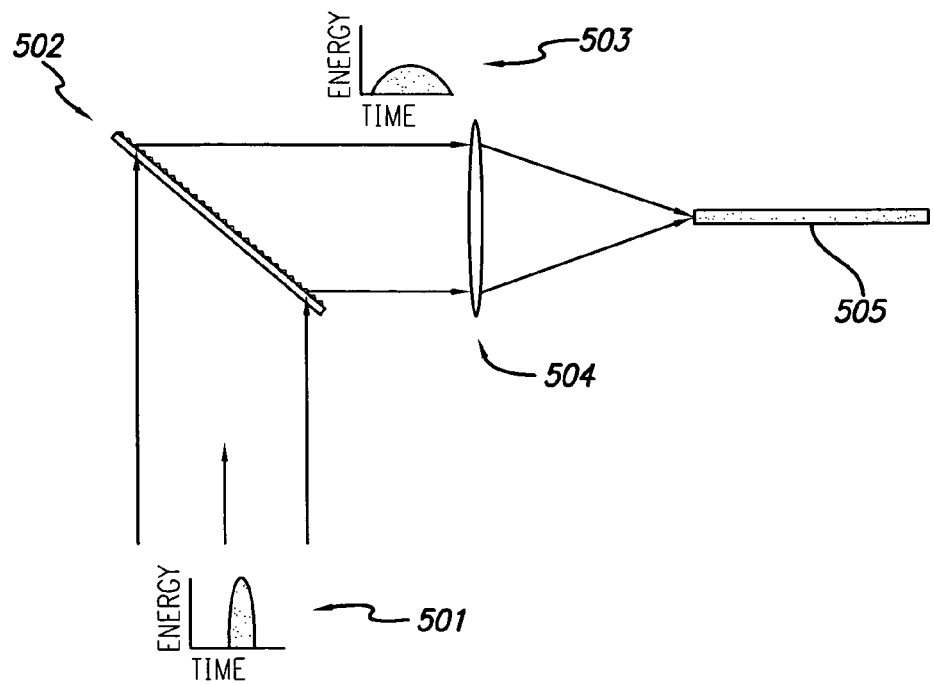
FIG. 5 illustrates an example of energy spreading using a single grating where the initial pulse leaving the laser occurs over a relatively short period of time and exhibits higher peak power.

Spreading the energy of the pulse in time maintains the total energy of the pulse but can diminish peak power. FIG. 5 illustrates an example of energy spreading using a single grating where the initial pulse 501 leaving the laser occurs over a relatively short period of time and exhibits higher peak power. The initial pulse 501 may pass through a grating 502. The subsequent pulse 503 occurs over a longer period of time and may have similar total energy but lower peak power. A focusing lens 504 may focus the pulsed laser beam into a fiber amplifier 505. More than one grating may be employed in addition to reflective surfaces such as mirrors in multiple pass or multiple pulse configurations.

To achieve energy spreading, the present design may illuminate the specimen, such as a wafer or photomask, by pumping a laser oscillator to generate coherent light, mode-locking or q-switching the laser oscillator to create a pulsed output beam, expanding the pulses of the pulsed output beam, and amplifying the coherent light with at least one fiber laser amplifiers. Note that in this arrangement multiple laser oscillators may be employed and pumped using the foregoing design. Mode locking and q-switching are laser techniques known to those skilled in the art, but in general, mode locking comprises modulating laser energy content for each mode within the laser to selectively produce energy bursts having desired properties. Q-switching may be employed in the optical resonator portion of a laser device to prevent lasing action until a relatively high level of inversion (optical gain and energy storage) may be achieved in the lasing medium.

Figure 6:
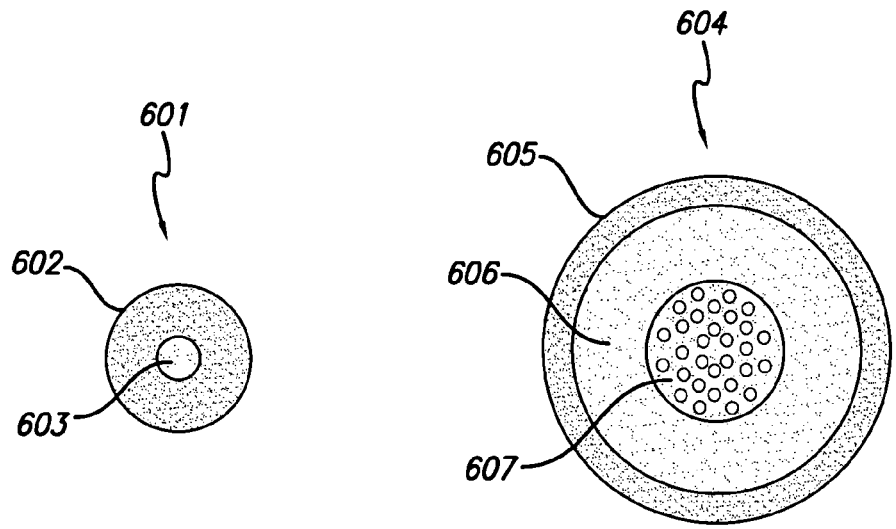
FIG. 6 is a hybrid photonic crystal fiber into the fiber laser amplifier using pump cladding.

The second technique used to avoid non-linear effects in the fiber laser amplifier is increasing the mode area. The present design may incorporate a hybrid photonic crystal fiber into the fiber laser amplifier 202 using pump cladding as shown in FIG. 6. For purposes of comparison, FIG. 6 shows a traditional single-mode fiber 601 which allows a beam with a small single mode. The traditional single-mode fiber 601 has a relatively small doped fiber core 603 with external cladding 602. The hybrid photonic crystal fiber with pump cladding 604 allows a larger single-mode beam to propagate and may include a doped fiber core having a photonic crystal structure 607, pump cladding 606, and external cladding 605.

Figure 7:
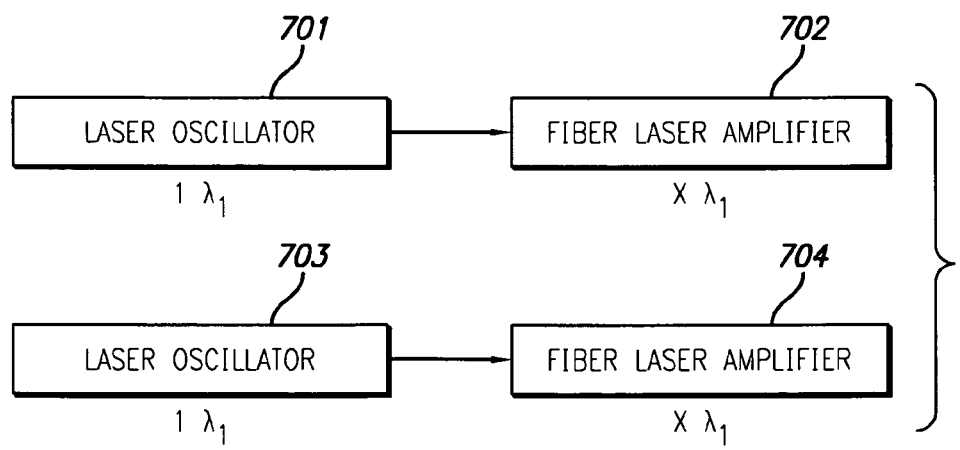
FIG. 7 shows an illuminator containing a plurality of fiber laser amplifiers each having similar output frequency values.

Multiple fiber amplifier illuminators can provide increased power or an increased number of available wavelengths. FIG. 7 shows an illuminator containing a plurality of fiber laser amplifiers each having similar output frequency values. From FIG. 7, the illuminator may include two laser oscillators 701 and 703 and two fiber laser amplifiers 702 and 704. Both laser oscillators 701 and 703 generate similar central frequencies $\lambda_1$, where the subscript "1" indicates that the output power of the laser oscillators 701 and 703 is not amplified. Both fiber laser amplifiers 702 and 704 amplify light having substantially the same frequency. The letter "X" before $\lambda_1$ indicates the amplifier has multiplied the intensity of the laser's output power by a factor.

Figure 8:
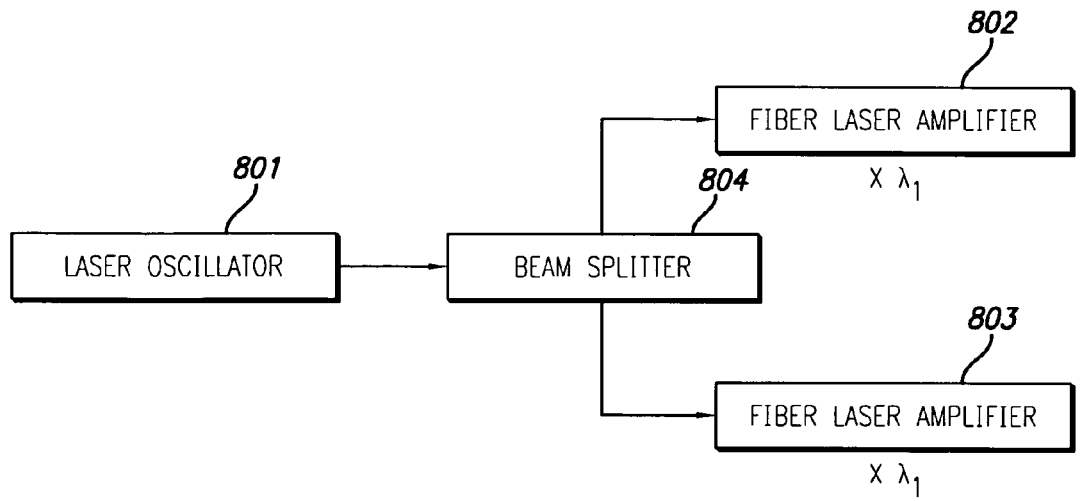
FIG. 8 illustrates a plurality of fiber laser amplifiers with substantially the same output frequency in a different configuration.

FIG. 8 also illustrates a plurality of fiber laser amplifiers with substantially the same output frequency in a different configuration. From FIG. 8, the illuminator may include one laser oscillator 801 feeding two fiber laser amplifiers 802 and 803. Both laser amplifiers 802 and 803 amplify substantially the same frequency. The configuration of FIG. 8 may require a beam splitter 804 or another device to deliver output light from the laser oscillator 801 to the two fiber laser amplifiers 802 and 803. The configurations in FIGS. 7 and 8 can increase the available power or provide multiple channels of light with substantially the same frequency to allow bright-field imaging and dark-field imaging within the same inspection system.

Figure 9:
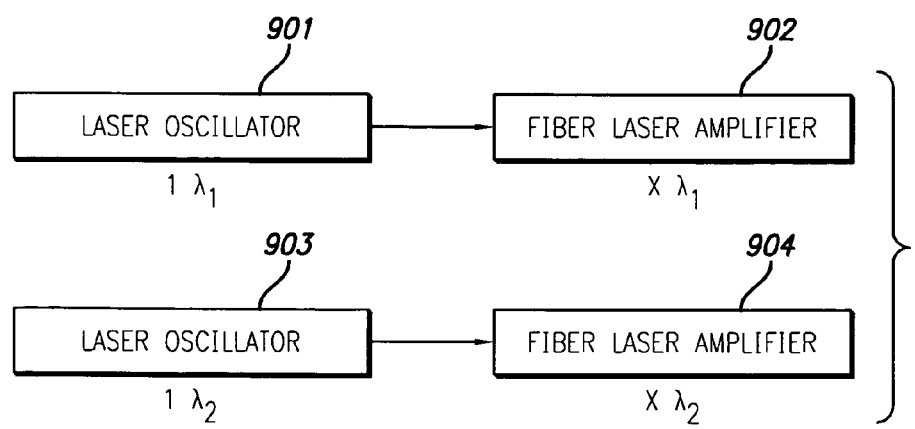
FIG. 9 shows an illuminator comprising multiple fiber laser amplifiers, with certain fiber laser amplifiers have different output frequencies.

FIG. 9 shows an illuminator comprising multiple fiber laser amplifiers, with certain fiber laser amplifiers have different output frequencies. FIG. 9 shows an illuminator with two laser oscillators 901 and 903 and two fiber laser amplifiers 902 and 904. Both laser oscillators 901 and 903 generate similar central frequencies ($\lambda_1$). The first fiber laser amplifier 902 may selectively amplify one frequency, $\lambda_1$, within the gain bandwidth of the first laser oscillator 901, and the second fiber laser amplifier 904 selectively amplifies a different frequency $\lambda_2$ within the gain bandwidth of the second laser oscillator 903.

Figure 10:
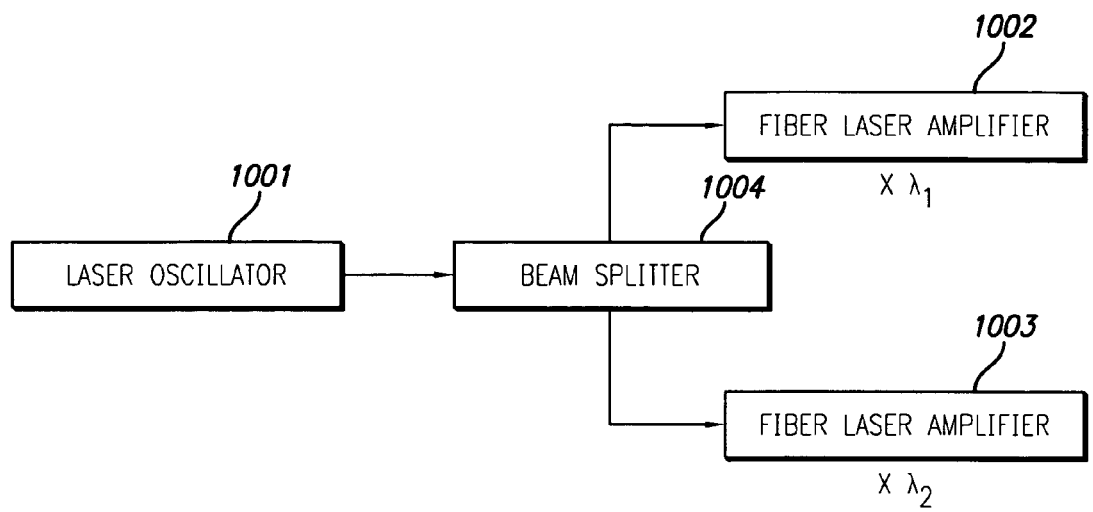
FIG. 10 illustrates an alternate configuration of a plurality of fiber laser amplifiers having different output frequencies.

FIG. 10 illustrates an alternate configuration of a plurality of fiber laser amplifiers having different output frequencies. FIG. 10 shows an illuminator with one laser oscillator 1001 and two fiber laser amplifiers 1002 and 1003. The first fiber laser amplifier 1002 selectively amplifies light having one frequency $\lambda_1$ within the gain bandwidth of the laser oscillator 1001. The second fiber laser amplifier 1003 selectively amplifies light having a different frequency $\lambda_2$ within the gain bandwidth of the same laser oscillator 1001. This alternate configuration can employ a beam splitter 1004 or another device for delivering the output light from the laser oscillator 1001 into two fiber laser amplifiers 1002 and 1003. The configurations in FIGS. 9 and 10 can facilitate inspection of layers with different materials and different thicknesses.

The devices of FIGS. 9 and 10 may be employed to illuminate a specimen, such as a wafer or photomask, by pumping the laser oscillator to generate a beam of coherent light, splitting said beam of coherent light into a plurality of sub-beams, and amplifying the sub-beams of coherent light using multiple fiber laser amplifiers. Alternately, the fiber laser amplifiers may amplify the same or a similar frequency within the gain bandwidth of the laser oscillator. Another embodiment may entail each of the fiber laser amplifiers amplifying a different frequency within the gain bandwidth of the laser oscillator.

In general, any number of laser oscillators and fiber laser amplifiers may be employed in configurations similar to those of FIGS. 7-10, and such designs may encounter certain tradeoffs in cost and performance.

The laser oscillator 201 may be virtually any type of laser, such as a solid-state laser or a semiconductor diode laser. Semiconductor lasers typically have output power of a few hundred milliwatts and a central wavelength of 600 to 900 nm.

High resolution inspection of small features on wafers and photomasks can be enhanced by light with relatively short wavelengths. Certain types of inspection can require an illuminator having hardware for converting light frequency output by the fiber laser amplifier. Efficient frequency conversion generally requires relatively high peak power, and generating relatively high peak power may employ a device or devices for creating a q-switched or mode-locked pulse train.

Figure 11:
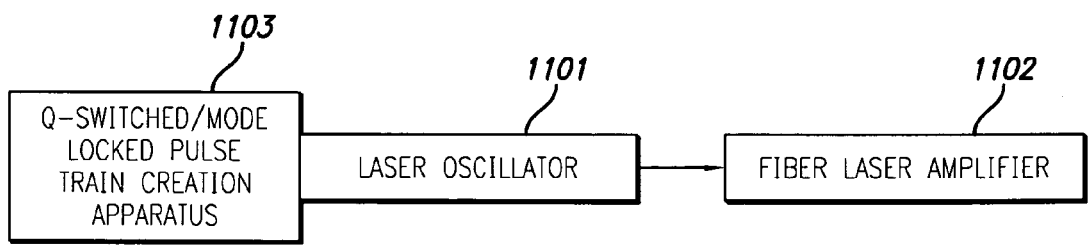
FIG. 11 shows an illuminator having a q-switched or mode-locked pulse train creation apparatus.

FIG. 11 shows an illuminator for an inspection system having at least one laser oscillator 1101, at least one fiber laser amplifier 1102, and q-switched or mode-locked pulse train creation apparatus 1103. Illumination using the device of FIG. 11 may comprise pumping the laser oscillator to generate coherent light, mode-locking or q-switching said laser oscillator or laser oscillators to create a pulsed output beam, and amplifying the coherent light with one or more fiber laser amplifiers.

High peak power is generally useful for efficient frequency conversion, but peak power in the beam is inversely proportional to the repetition rate. Thus a relatively low repetition rate generates a relatively high peak power. A high repetition rate can enhance the performance of a time domain integration (TDI) sensor, used to capture signals reflected from the specimen or through the specimen.

Creating a q-switched or mode-locked pulse train 1103 may employ a passive device or an active device. A passive device could be, for example, a saturable absorber fabricated from either a semiconducting material or carbon nanotubes. An active device could be, for example, an acousto-optic modulator, an electro-optic modulator, an active mirror with controlled reflectivity, or an electronic switch.

Figure 12:
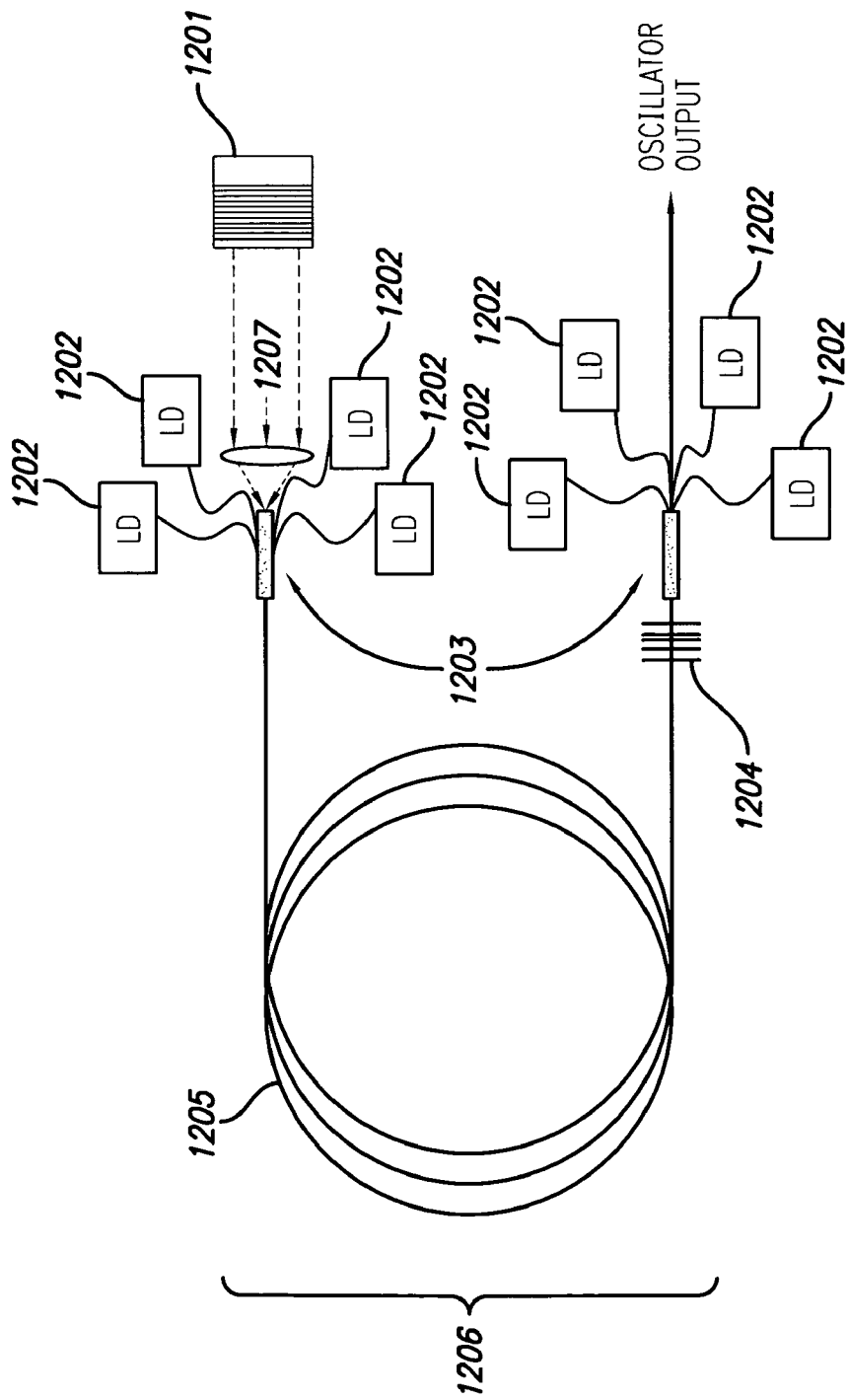
FIG. 12 shows a fiber laser oscillator.

FIG. 12 shows a fiber laser oscillator 1206, where the bracket indicates that all the components to the right of the bracket collectively make up the fiber laser oscillator. One mirror may be a saturable absorber 1201 producing a q-switched or mode-locked pulse. The saturable absorber 1201 may be a Bragg reflector made from semiconducting material, typically a gallium arsenide heterostructure with in the range of approximately 50 to 80 layers, alternately n-doped and p-doped, that change from absorptive to reflective over short time scales when receiving light from a continuous-wave laser. A collimating lens 1207 may be positioned between the saturable absorber 1201 and the doped fiber 1205 or the saturable absorber 1201 may be affixed directly to the doped fiber 1205.

The saturable absorber 1201 may generally deliver a repetition rate ranging from approximately 5 to over 100 MHz, depending on the length of the fiber. As long as the saturable absorber 1201 operates faster than the round trip time of the cavity, the length of cavity determines the repetition rate. In this arrangement, a fiber length of 1.875 meters generally yields a repetition rate of somewhere in the range of about 80 MHz.

The second mirror of the fiber laser oscillator 1206 is an output grating 1204. Multiple laser diodes 1202 may pump the gain medium, a doped fiber 1205 surrounded by pump cladding. A pump combiner 1203 may direct light from the laser diodes 1202 into the pump cladding surrounding the doped fiber 1205.

Figure 13:
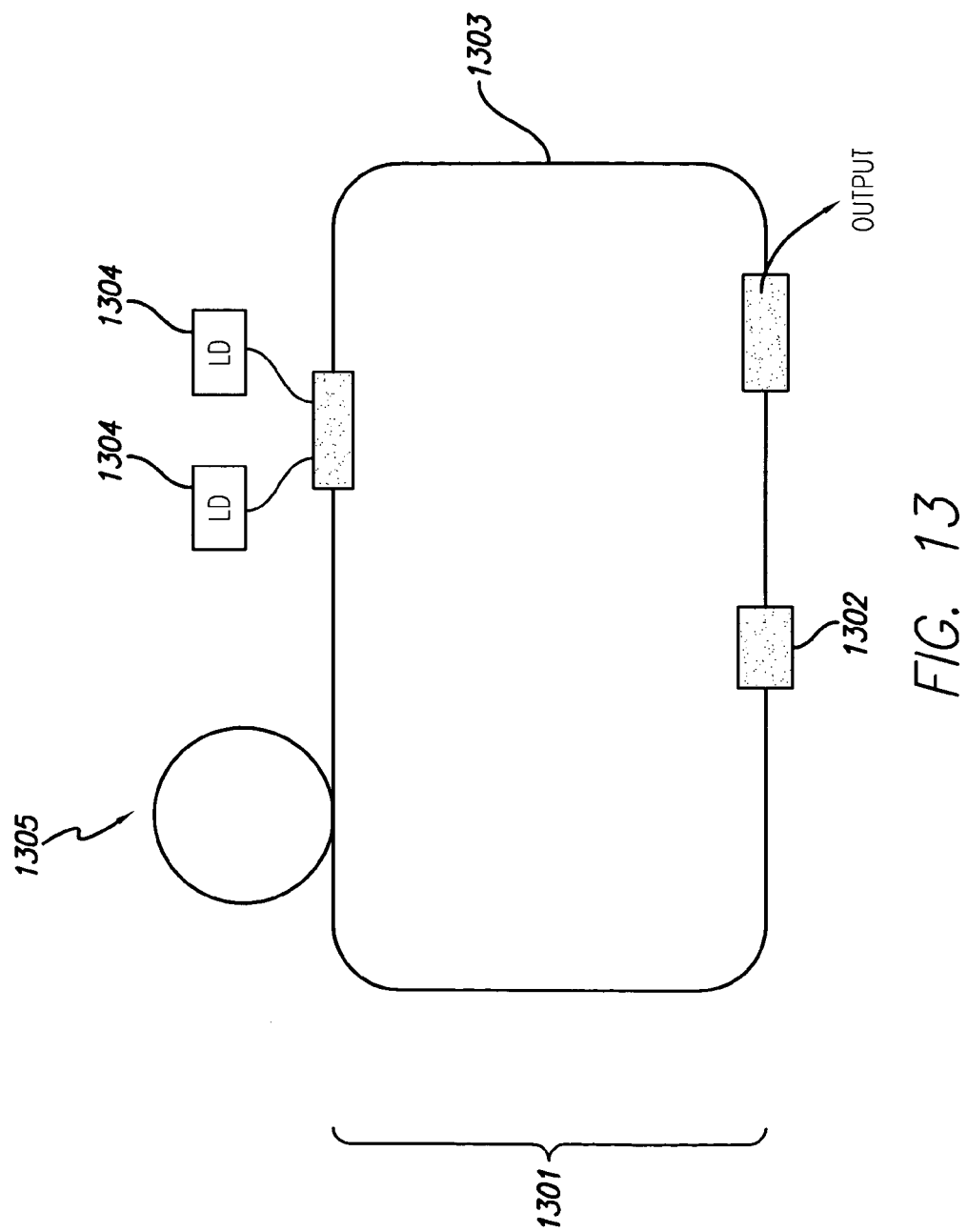
FIG. 13 shows a fiber laser configured in a ring with an active intensity modulator.

FIG. 13 shows an example of a fiber laser oscillator 1301 configured in a ring with an active intensity modulator 1302. The fiber ring resonator 1303 may include optical fiber with pump cladding. Two laser diodes 1304 provide pump energy. Doped fiber 1305 may be provided as shown.

The present design may illuminate by pumping one or more fiber laser oscillators to generate coherent light. Fiber laser oscillators tend to be relatively compact and inexpensive. The illuminator may include one or more laser oscillators and one or more fiber laser amplifiers, where at least one laser oscillator is a fiber laser oscillator. For example, one or more of the laser oscillators 201 of FIG. 2 could be a fiber laser oscillator. The present design may include a combined fiber laser oscillator and fiber laser amplifier. Such a design may pump at least one fiber laser oscillators to generate coherent light and amplify the coherent light using one or more fiber laser amplifiers. The combination of the fiber laser oscillator and the fiber amplifier tends to provide relatively high power and high beam quality.

An illuminator having at least one fiber laser oscillator and at least one fiber laser amplifier may include one or more laser diodes 1202 as the pumping system for the fiber laser oscillator. Current individual laser diodes 1202 typically generate energy in the range of 1 to 5 watts. A bar or arrangement of laser diodes 1202 can generate in the range of 10 to 40 watts. The laser diodes 1202 may produce light energy at a wavelength near the absorption peak of the optical fiber. The pump diodes may emit light having a shorter wavelength than the fiber laser oscillator.

Figure 14:
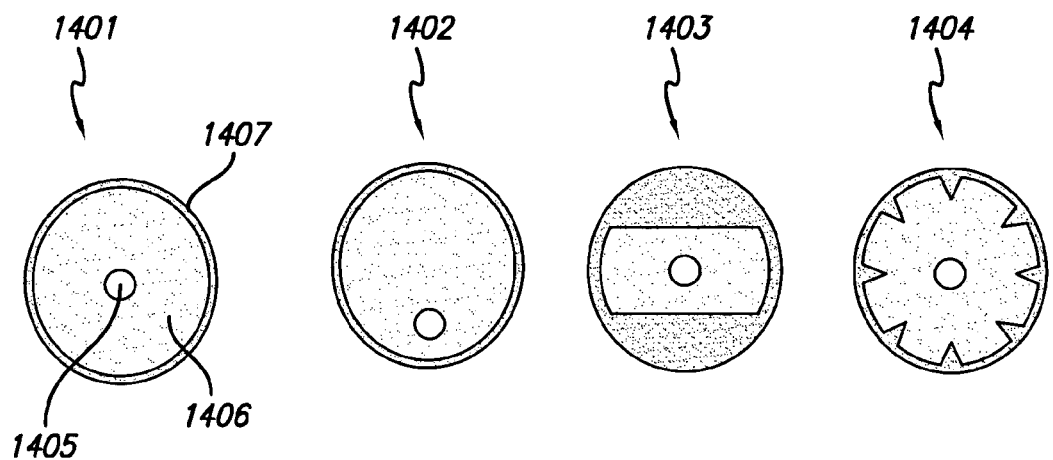
FIG. 14 shows four cross sections of optical fiber incorporating pump cladding.

A closely related design is an illuminator for an inspection system comprising a fiber laser oscillator and a fiber laser amplifier in which either the fiber laser oscillator or the fiber laser amplifier incorporates pump cladding. FIG. 14 shows four cross sections 1401, 1402, 1403, 1404 of optical fiber incorporating pump cladding. In each cross section, an internal white circle represents the doped fiber core 1405. The dark or black area represents the external cladding 1407. The intermediate or gray area represents pump cladding 1406.

Pump cladding 1406 includes optical fiber without doping to allow pump light to propagate. The pump cladding 1406 guides the pump light down the length of the fiber. The pump light reflects through the doped fiber core 1405 multiple times, increasing the probability that the doped fiber core 1405 will absorb the pump light. The pump cladding 1406 facilitates uniform absorption throughout the length of the doped fiber core 1405. Absorption can be improved by positioning the doped fiber core 1405 away from the center of the fiber assembly as shown in cross section 1402. Asymmetrical optical fiber configurations 1403 and 1404 can provide increased absorption relative to over the symmetrical configuration of cross section 1401.

Figure 15:
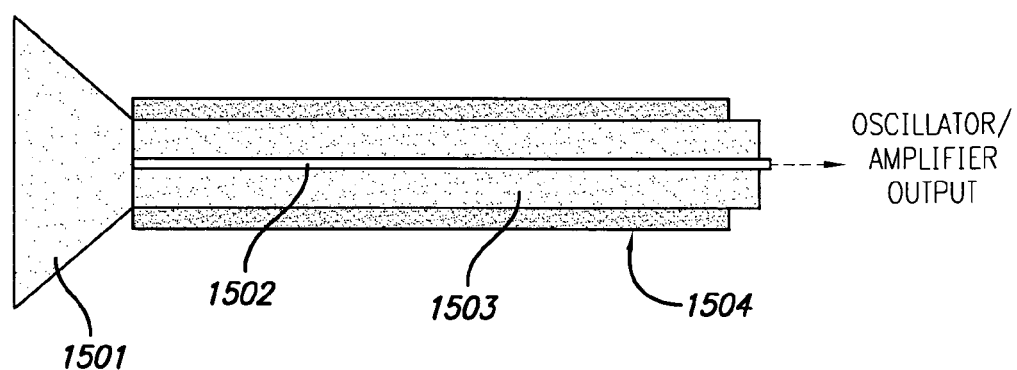
FIG. 15 is one example of end pumping.

Using this arrangement, illumination may include pumping a fiber laser oscillator to generate coherent light and amplifying the coherent light using one or more fiber laser amplifiers. Pumping may include pumping the fiber laser oscillator using pump cladding. Pump light may be injected into the fiber laser oscillator by pumping light from the end of the oscillator. FIG. 15 shows one example of end pumping. The input pump light 1501 enters the fiber laser oscillator at the left. The cross sectional diagram shows the highest-index doped fiber core 1502, the white region at the center, the middle-index pump cladding 1503, the intermediate or gray region surrounding the doped fiber core, and the low-index outside cladding 1504 represented by the dark or black region on the outside of the fiber. The pump cladding 1503 can enhance pump laser photon absorption and increase the spatial uniformity of absorption throughout the fiber laser oscillator. Note that FIG. 12 also illustrates end pumping of a fiber laser oscillator using pump cladding. Several laser diodes 1202 contribute pump energy and pump combiners 1203 direct energy into the pump cladding. End pumping may apply to the fiber laser amplifier as well as the fiber laser oscillator.

Figure 16:
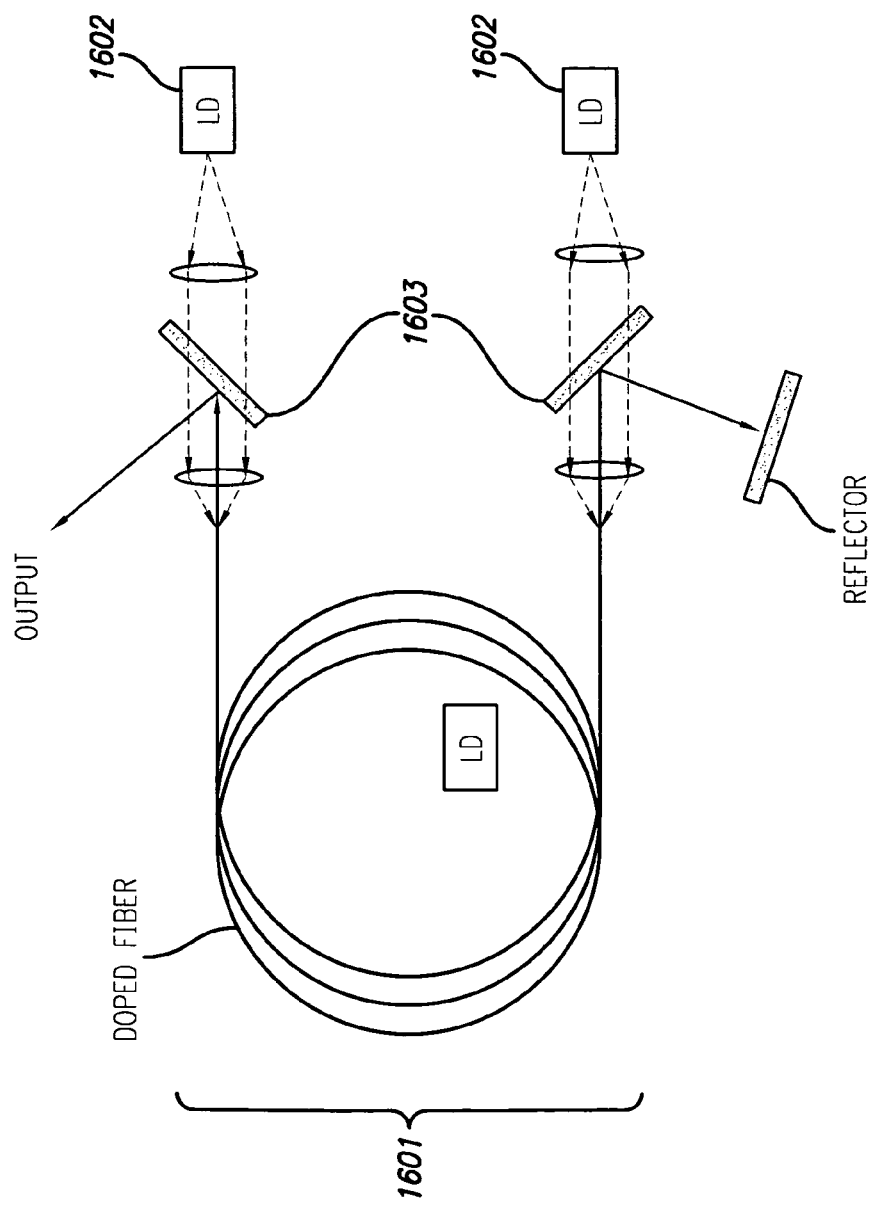
FIG. 16 is a fiber laser oscillator where laser diodes pump the fiber from the end without the use of a pump combiner.

FIG. 16 shows a diagram of a fiber laser oscillator or amplifier 1601 where laser diodes 1602 pump the fiber from the end without the use of a pump combiner. Dichroic mirrors 1603 may be employed to separate the pump light from the light originating within the fiber.

Figure 17:
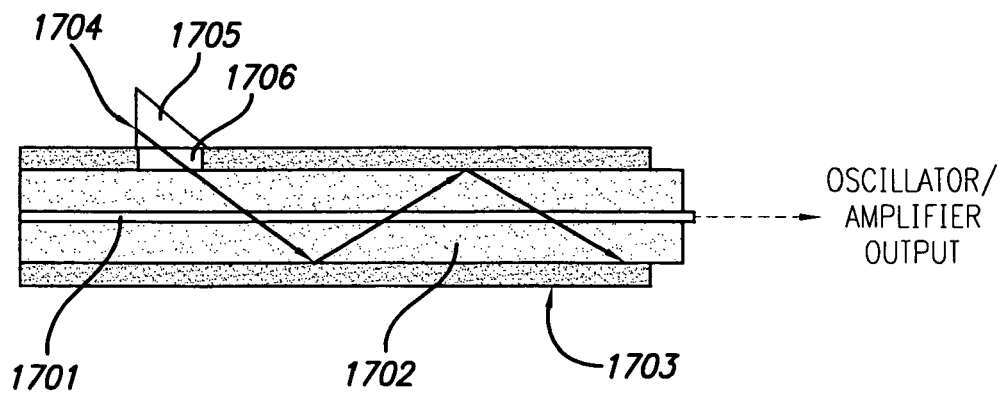
FIG. 17 illustrates laser oscillator pumping from the side.

Pump light may alternately be injected into the fiber laser oscillator from the side. FIG. 17 illustrates one embodiment of pumping from the side. The pump diode input 1704 enters the fiber laser oscillator at the upper left through a prism 1705 and an index-matching fluid or a mechanical coupling 1706. The index of refraction of the prism 1705 may match or approximate the index of refraction of the pump cladding 1702. The index-matching fluid 1706 may replace air between the prism 1705 and the pump cladding 1702 to minimize reflections.

The design may employ a fiber Bragg grating as the grating 1204 in FIG. 12, serving as the output coupling mirror for the fiber laser oscillator. In such a design, at least one mirror in the fiber laser oscillator may include a grating. The design of the grating significantly influences the reflectivity of the mirror or reflective surface, as the greater the number of periods in the mirror, the greater the reflectivity. The grating can also filter the fiber laser oscillator's broadband light. The spacing between the periods determines those frequencies within the fiber's gain bandwidth experiencing gain. Such a design enables the fiber laser oscillator to have narrowband output.

The grating can also control the group velocity dispersion of light, thereby breaking up the pulses to lower the peak power of the light entering the amplifier. Lowering the peak power of the light entering the amplifier can keep the amplifier operating linearly. The grating may also operate so that the fiber laser oscillator emits light at several discrete narrowband wavelengths. In this way, a single fiber laser oscillator can provide numerous inspection wavelengths. The illuminator may therefore include a grating employing different grating frequencies.

Figure 18:
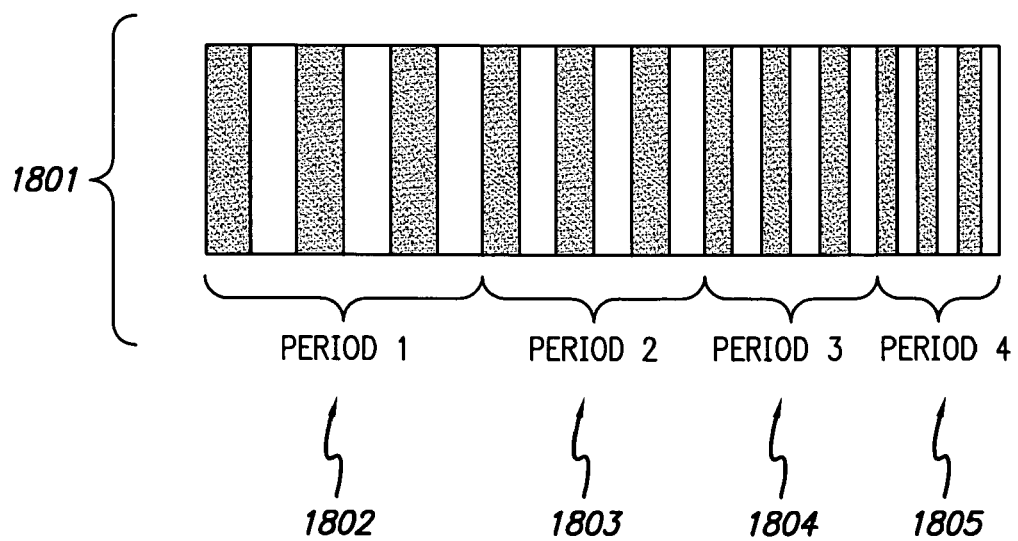
FIG. 18 shows a grating with different grating frequencies, with multiple instances of four periods.

FIG. 18 shows a grating 1801 with different grating frequencies, with multiple instances of four periods 1802, 1803, 1804, and 1805. A grating of this type can cause the fiber laser oscillator to emit four discrete wavelengths of narrowband light within the oscillator gain bandwidth, each discrete wavelength corresponding to one of the four periods.

The grating may allow the fiber laser oscillator to emit broadband light. Such a construction includes a fiber laser oscillator having a chirped grating, such as the chirped grating 1901 of FIG. 19. Such a construction can provide a continuously varying period, causing the fiber laser oscillator to have broadband output.

In certain applications, such as those benefiting from short-wavelength light energy, light may be transmitted through a frequency conversion crystal. A frequency conversion crystal provide phase-matching for light energy exhibiting a single degree of polarization. In such a design, the illuminator may include a fiber laser oscillator having a polarization-preserving fiber. FIG. 20 illustrates one type of polarization-preserving fiber having a solid core. The white region at the center is the doped fiber core 2004. The gray or intermediate region surrounding the doped fiber core 2004 is the pump cladding 2003. The black or dark region surrounding the pump cladding is the external cladding 2002. The structure also contains a different material 2001 having either asymmetrical structure or is constructed to reduce the symmetry of the cross section of the solid core. The different material 2001 creates internal stresses which render the solid core birefringent, resulting in the fiber favoring light of one polarization. The different material 2001 may be, for example, a glass or a polymer.

FIG. 21 illustrates two cross sections of polarization-preserving photonic crystal fiber 2101 and 2102. Within the cross section of the first fiber 2101, FIG. 21 depicts the doped fiber core 2106, air cladding 2105, and the external cladding 2104. The fiber may contain another material 2103 with an asymmetrical structure. Within the cross section of the second fiber 2102, the air channels may be arranged asymmetrically. Both these configurations 2101 and 2102 cause the photonic crystal fiber to favor light of a single polarization. Light energy polarization may therefore be controlled in the fiber laser oscillator or the fiber laser amplifier.

More than one fiber laser oscillator may be used in the design. Multiple fiber laser oscillators with the same wavelength may be used to increase the available power or provide separate channels for bright-field and dark-field imaging. Thus in the illuminator, the fiber laser oscillators may have the same or similar emission wavelengths.

Figure 22:
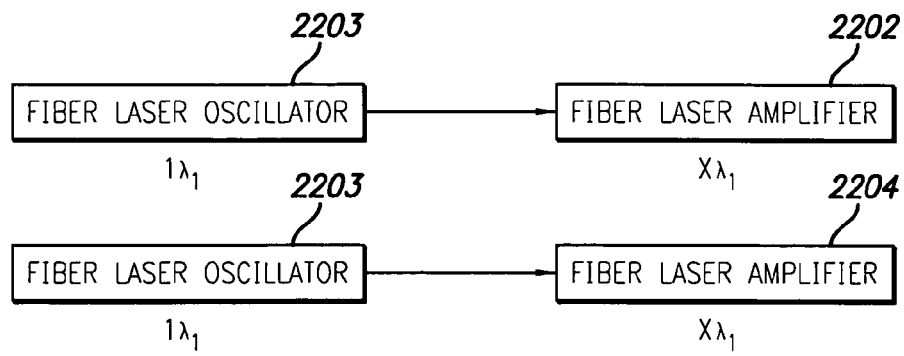
FIG. 22 shows two fiber laser oscillators and two fiber laser amplifiers all employing the same or similar wavelengths.

FIG. 22 illustrates two fiber laser oscillators 2201 and 2203 and two fiber laser amplifiers 2202 and 2204. Both fiber laser oscillators 2201 and 2203 have the same emission wavelength ($1\lambda_1$), and both fiber laser amplifiers have the same emission wavelength ($X\lambda_1$). The "1" subscript indicates that the output power from the fiber laser oscillators 2201 and 2203 is unamplified. The "X" value indicates that output power from the fiber laser amplifiers 2202 and 2204 is amplified by a value of X.

Figure 23:
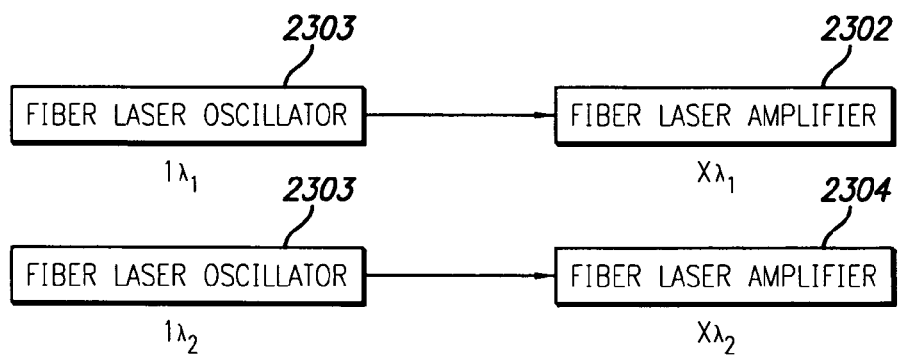
FIG. 23 is two fiber laser oscillators and two fiber laser amplifiers using different wavelengths.

FIG. 23 shows two fiber laser oscillators 2301 and 2303 and two fiber laser amplifiers 2302 and 2304. Both fiber laser oscillators 2301 and 2303 have the same or similar emission wavelengths ($1\lambda_1$). The first fiber laser amplifier 2302 may amplify one wavelength ($X\lambda_1$) within the gain bandwidth of the first fiber laser oscillator 2301, and the second fiber laser amplifier 2304 may amplify a different wavelength ($X\lambda_2$) within the gain bandwidth of the second fiber laser oscillator 2303. Two fiber laser oscillators may provide the ability to mix output beams to generate coherent light at a third frequency.

Figure 24:
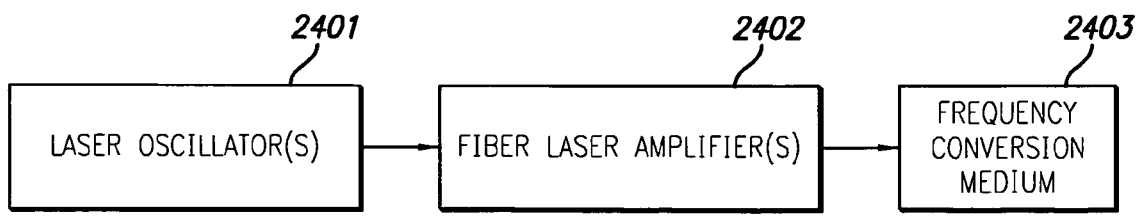
FIG. 24 illustrates an illuminator comprising a laser oscillator, a fiber laser amplifier, and a frequency conversion medium.

High-resolution inspection of small features on state-of-the-art wafers and photomasks may require light with a wavelength near the wavelength of the wafer exposure tool, which can be 198 nm or 248 nm. Inspection systems employing fiber optic gain media can benefit from an illuminator with a frequency conversion medium. FIG. 24 shows an illuminator comprising a laser oscillator 2401, a fiber laser amplifier 2402, and a frequency conversion medium 2403.

Figure 25:
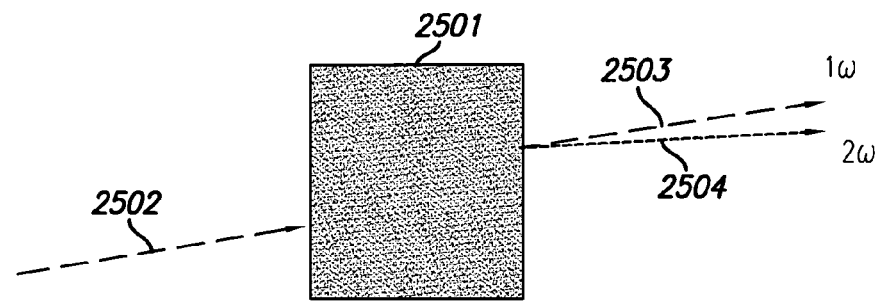
FIG. 25 shows a birefringent crystal with input light entering the crystal.

The frequency conversion medium could be a nonlinear crystal such as lithium niobate, beta barium borate, lithium barium borate, cesium lithium barium borate, or other birefringent crystals. FIG. 25 shows a birefringent crystal 2501 with input light 2502 entering the crystal. Frequency-converted light 2504 and non-frequency-converted light 2503 exit from the crystal.

Figure 26:
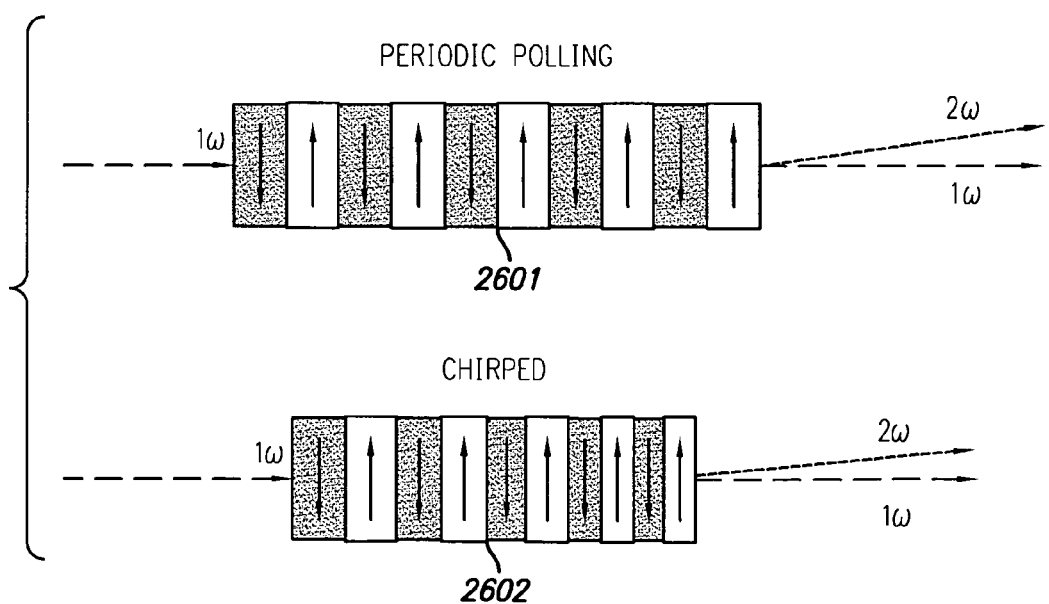
FIG. 26 shows a periodically polled ferromagnetic material where the orientation of the magnetic domains alternates in successive regions.

The frequency conversion medium could also be a periodically polled material such as periodically polled lithium niobate, magnesium strontium lithium niobate, $BaMgF_4$, or a material from the KTP family ($MTiOXO_4$, where M is K, Rb, or Cs and X is P or As). FIG. 26 shows a periodically polled ferromagnetic material where the orientation of the magnetic domains alternates in successive regions. At the top 2601 of the periodically polled material, the dimensions of the periods are consistent. In the periodically polled material at the bottom 2602, the dimensions of the period change along the length of the material, or the periodic poling is "chirped." A periodically polled crystal in which the domains are "fanned" (wedge-shaped) may be provided as an alternate to a crystal that is chirped. Other types of frequency conversion media may be provided depending on the application.

Locating the fiber laser amplifier and frequency conversion medium in different places can provide certain benefits, including the inability of waste heat from the fiber laser amplifier and associated pump diodes to compromise the optics thermal stability, and effective space utilization.

Figure 27:
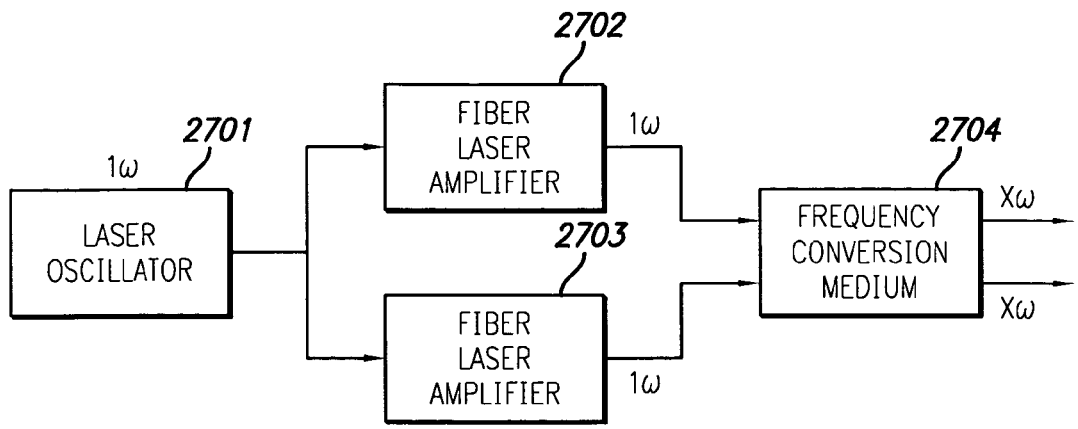
FIG. 27 shows a single laser oscillator feeding two fiber laser amplifiers.
Figure 28:
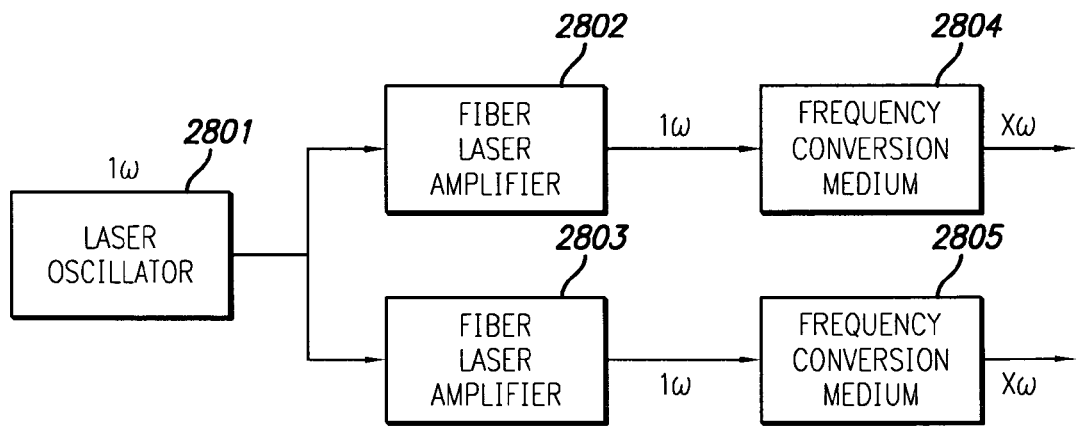
FIG. 28 is an illuminator including a laser oscillator feeding two fiber laser amplifiers, both amplifying the same or similar frequencies.

FIGS. 27 through 30 illustrate various configurations of laser oscillators, fiber laser amplifiers, and frequency conversion media. FIG. 27 shows a single laser oscillator 2701 feeding two fiber laser amplifiers 2702 and 2703. The amplified light from both fiber laser amplifiers 2702 and 2703 may enter the same frequency conversion medium 2704. The design of FIG. 27 may provide extra amplification before the frequency conversion step. FIG. 28 shows an illuminator including a laser oscillator 2801 feeding two fiber laser amplifiers 2802 and 2803, both amplifying the same or similar frequencies. Each fiber laser amplifier may feed a single frequency conversion medium. The first fiber laser amplifier 2802 may feed one frequency conversion medium 2804, while the second fiber laser amplifier 2803 may feed another frequency conversion medium 2805. Such a design can provide two frequency-doubled beams exhibiting the same or similar wavelengths, and may be employed in an inspection system allowing both dark-field and bright-field inspection with high resolution.

Figure 29:
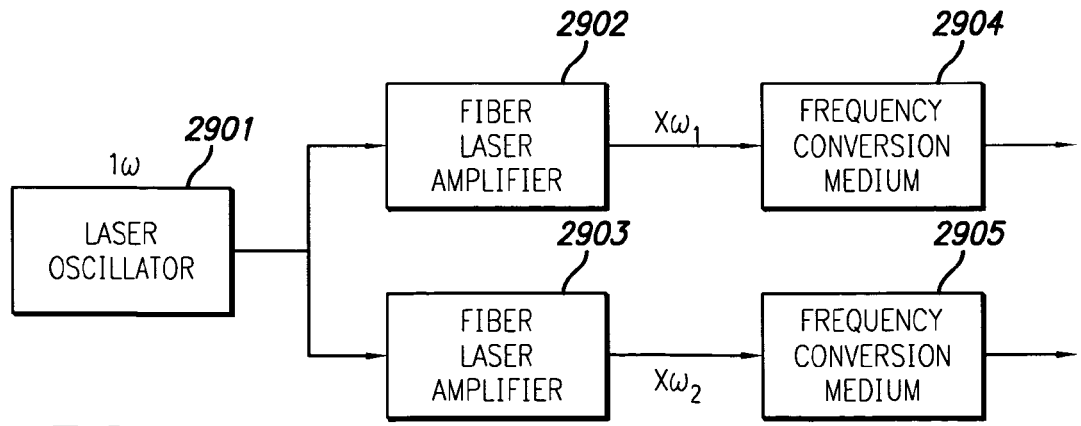
FIG. 29 shows an illuminator having a laser oscillator feeding two fiber laser amplifiers, each amplifying a different wavelength within the gain bandwidths of the laser oscillator.

FIG. 29 shows an illuminator having a laser oscillator 2901 feeding two fiber laser amplifiers 2902 and 2903, each amplifying a different wavelength within the gain bandwidths of the laser oscillator. Each fiber laser amplifier may feed its own frequency conversion medium. Fiber laser amplifier 2902 may feed frequency conversion medium 2904, while fiber laser amplifier 2903 may feed frequency conversion medium 2905, providing two frequency-doubled beams with different wavelengths.

Figure 30:
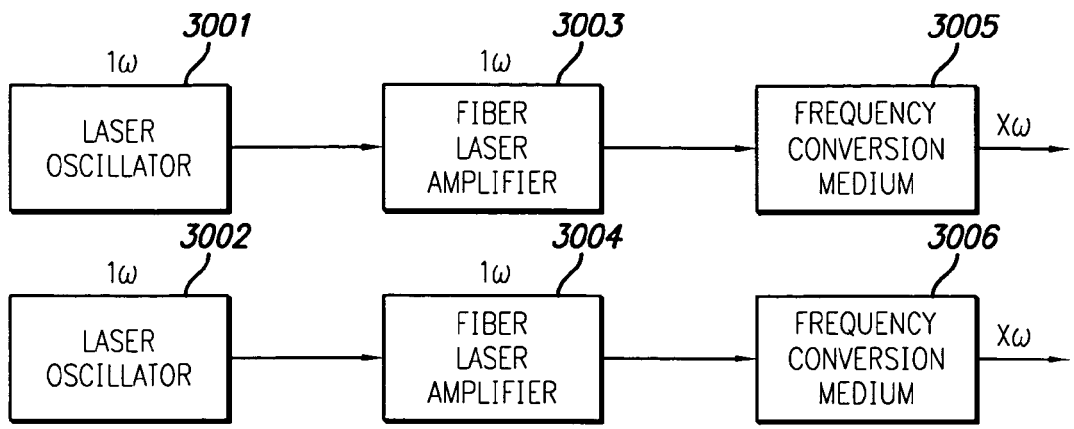
FIG. 30 illustrates an illuminator having two laser oscillators, two fiber laser amplifiers, and two frequency conversion media.

FIG. 30 shows an illuminator having two laser oscillators 3001 and 3002, two fiber laser amplifiers 3003 and 3004, and two frequency conversion media 3005 and 3006. Both laser oscillators emit the same or similar wavelengths, and both fiber laser amplifiers amplify the same or similar wavelengths. This configuration provides extra power for the inspection system or enables the inspection system to provide one frequency-doubled beam for a bright-field inspection and another frequency-doubled beam with the same frequency for dark-field inspection.

Figure 31:
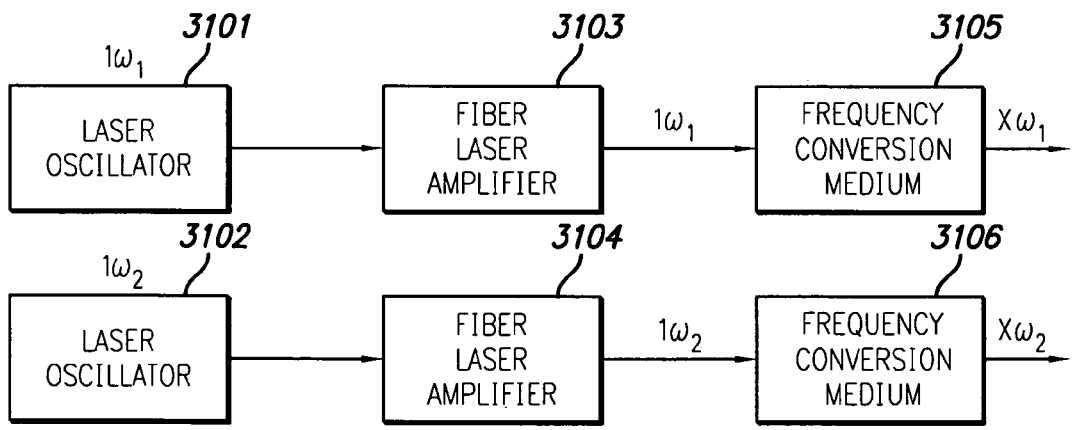
FIG. 31 shows an illuminator having two laser oscillators, two fiber laser amplifiers, and two frequency conversion media, where the two laser oscillators may emit different wavelengths.

FIG. 31 shows an illuminator having two laser oscillators 3101 and 3102, two fiber laser amplifiers 3103 and 3104, and two frequency conversion media 3105 and 3106. The two laser oscillators may emit different wavelengths. After the frequency conversion, the illuminator may provide two frequency-doubled beams with different wavelengths. This configuration may provide two wavelengths for high-resolution inspection.

Converting the frequency of coherent light can involve generating either a second harmonic, third harmonic, or fourth harmonic, or even higher harmonics. Multiple stages of frequency conversion may be beneficial. For example, the infra-red light exiting the fiber laser amplifier might enter a crystal of lithium barium borate or a periodically polled material. The frequency-doubled light exiting this first frequency doubling medium might enter a second frequency doubling medium, such as a crystal of beta barium borate or cesium lithium barium borate. The light exiting the second frequency conversion stage may have a wavelength near that of the wafer stepper or scanner. Fiber laser oscillators offer relatively sufficient pointing stability and emit a beam with a Gaussian profile.

Figure 32:
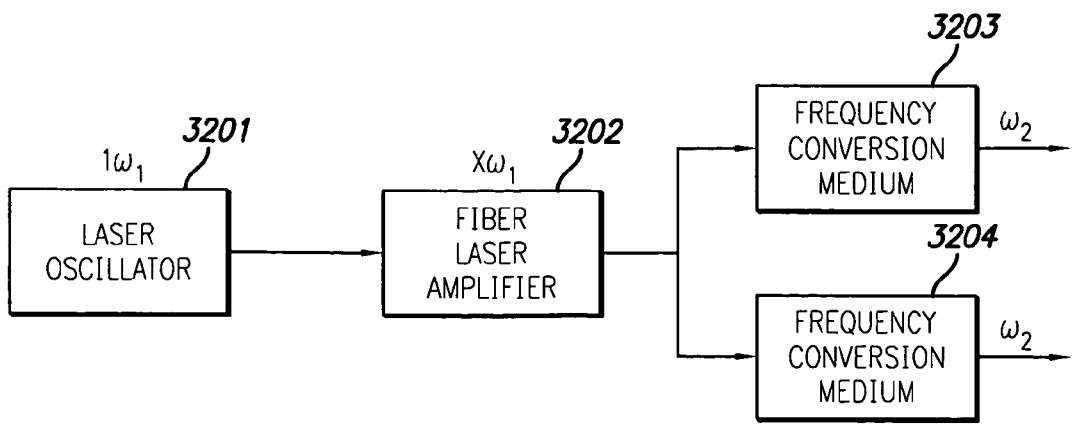
FIG. 32 represents a single laser oscillator feeding a single fiber laser amplifier, which then feeds two frequency conversion media.

Illuminating the wafer may therefore entail mode-locking or q-switching a laser oscillator, amplifying the resultant coherent light with at least one fiber laser amplifiers, and converting the frequency of the coherent light. FIG. 32 shows a single laser oscillator 3201 feeding a single fiber laser amplifier 3202, which then feeds two frequency conversion media 3203 and 3204. The design may illuminate by mode-locking or q-switching the laser fiber oscillator, amplifying the coherent light with a fiber laser amplifier, splitting the amplified beam into two or more sub-beams, and converting the frequency of each sub-beam.

Figure 33:
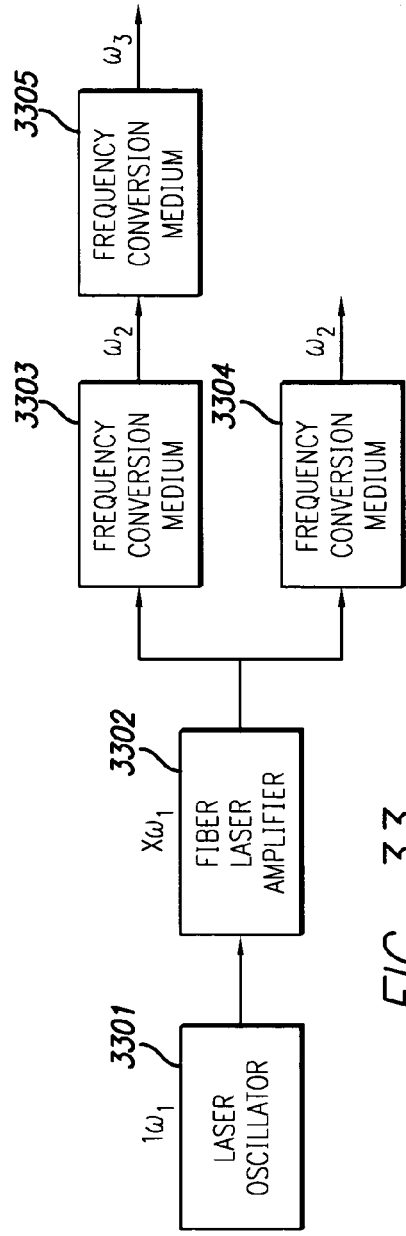
FIG. 33 shows a beam exiting from one frequency conversion medium and undergoing a second stage of frequency conversion in another frequency conversion medium.

The frequency of each sub-beam may be converted to the same frequency, as shown in FIG. 32, or to different frequencies, as shown in FIG. 33, where the beam exiting from one frequency conversion medium 3303 undergoes a second stage of frequency conversion in another frequency conversion medium 3305. In either case, the presence of multiple frequency-doubled beams offers unprecedented flexibility to the inspection system.

Figure 34:
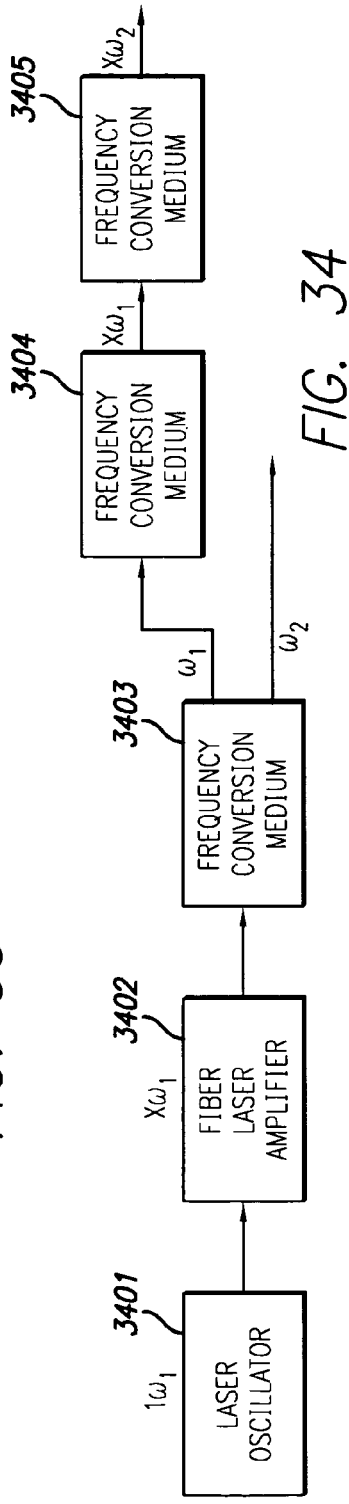
FIG. 34 illustrates light from a laser oscillator entering a fiber laser amplifier.

The frequency conversion medium converts only a portion of the incident light. The medium may emit some light with the doubled frequency and some unconverted light, called residual fundamental-frequency light. Amplifying this residual fundamental-frequency light may provide certain benefits, as may providing the amplified residual fundamental-frequency light to another frequency conversion crystal. FIG. 34 illustrates light from a laser oscillator 3401 entering a fiber laser amplifier 3402. The amplified light ($x\lambda_1$) may enter a frequency conversion medium 3403. Frequency-doubled light ($\lambda_2$) may exit the frequency conversion medium, as may residual fundamental-frequency light ($\lambda_1$). The residual fundamental-frequency light may enter a fiber laser amplifier 3404. Alternatively, the light leaving the fiber laser amplifier 3404 can enter another frequency conversion medium 3405.

Thus the present design may include amplifying residual fundamental-frequency light from the frequency conversion process using an additional fiber laser amplifier beyond those provided for in-line illumination purposes. Such a design may be enhanced by converting the frequency of the amplified residual fundamental-frequency light.

Frequency of the beam may be tuned by sending the beam through a crystal such as cesium lithium sapphire. If a cesium lithium sapphire crystal receives input light with a wavelength of 266 nm, the crystal can emit light with a wavelength from 266 nm to 320 nm, depending on the angular aspects associated with the crystal. Such a design enables tuning the frequency of frequency-converted light in the design described above.

Figure 35A:
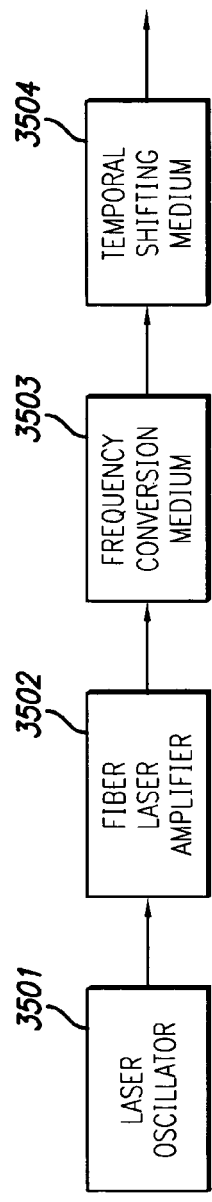
FIG. 35A shows a laser oscillator, a fiber laser amplifier, a frequency conversion medium, and a temporal shifting medium.
Figure 35B:
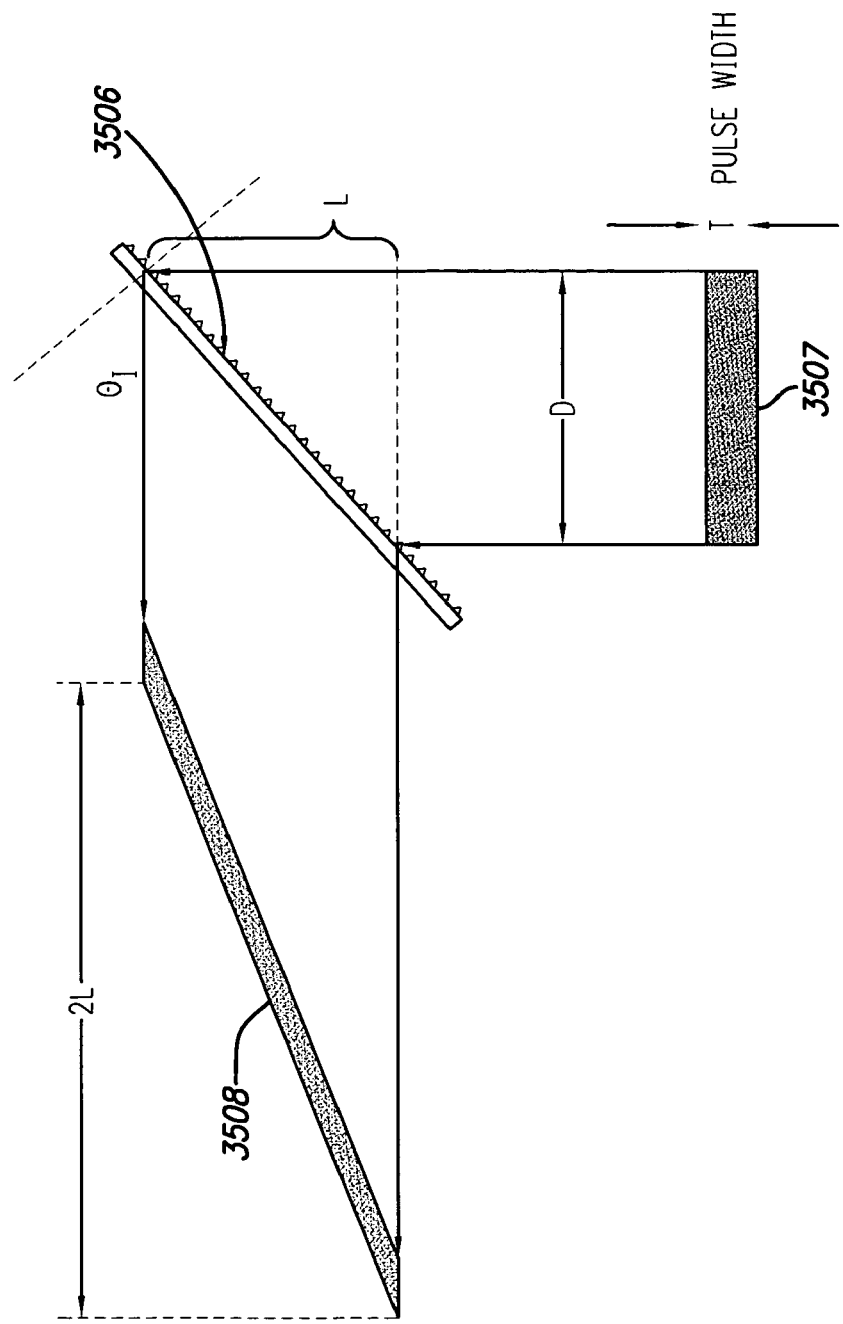
FIG. 35B shows a grating as a temporal shifting medium.

Birefringent crystals can convert the frequency of an incoming beam when the power of the beam exceeds a certain threshold. An amplifier may be provided to increase the power of the beam before frequency conversion. In some cases, hardware for lowering the peak power of the frequency-converted light may be provided to avoid harming the specimen. Such a design may therefore include a temporal shifting medium. A temporal shifting medium spreads out the illumination pulse in time, thereby diminishing its peak power. FIG. 35A shows a laser oscillator 3501, a fiber laser amplifier 3502, a frequency conversion medium 3503 and a temporal shifting medium 3504. The temporal shifting medium 3504 may take various forms, including but not limited to a grating, an etalon, one or more beam splitters, or a combination of beam splitters and reflective surfaces such as mirrors. From FIG. 35B, a grating 3506 can serve as a temporal shifting medium that effectively stretches the pulse in time. The input pulse 3507 with pulse width T may enter the grating 3506. The grating 3506 may delay one side of the outgoing pulse 3508 by the time required for light to travel the distance 2L, resulting in a lower peak power of the pulse.

Figure 36:
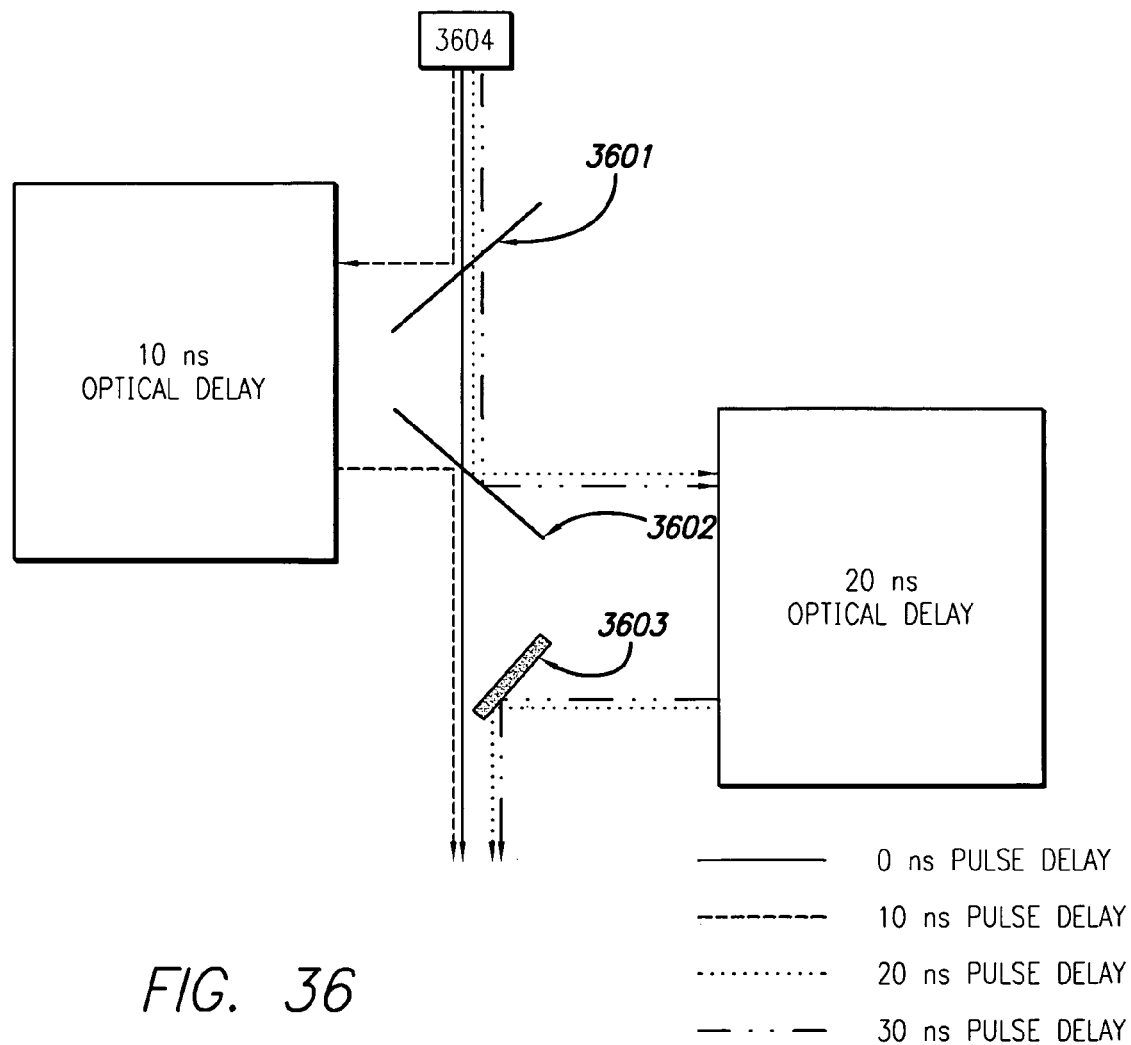
FIG. 36 illustrates beam splitters and one or more reflective surfaces serving as a temporal shifting medium.

FIG. 36 shows how beam splitters 3601 and 3602 and one or more reflective surfaces 3603 can serve as a temporal shifting medium. The beam enters FIG. 36 from a transmitting device 3604, such as a frequency conversion medium. The beam splitters 3601 and 3602 and reflective surface 3603 cause portions of each pulse to take different paths resulting in a 10-nanosecond delay, or a 20-nanosecond delay, or both (a 30-nanosecond delay). This arrangement divides and prolongs the pulse, thereby diminishing the peak power of the beam. If the delay exceeds the pulse width, the beam splitters can also divide a single pulse into a train of separate pulses. Such a design may be implemented using any number of beam splitters, with or without reflective surfaces.

Figure 37:
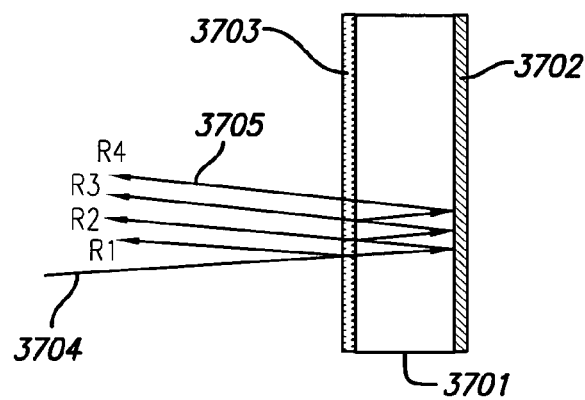
FIG. 37 shows an etalon serving as a temporal shifting medium.

FIG. 37 shows an etalon 3701 serving as a temporal shifting medium. The etalon 3701 in this design is a block of glass having a relatively high-reflectivity surface 3702 and a relatively low-reflectivity surface 3703. The incident pulse 3704 may strike the low-reflectivity surface 3703, and a portion of the light may reflect from the low-reflectivity surface 3703. The remainder of the light may pass through the low-reflectivity surface 3703, strike the high-reflectivity surface 3702, and reflect outward. The photons bounce back and forth within the etalon 3701 many times, a portion of the photons escaping each time. In this way, the etalon 3701 may divide a single pulse 3704 into a series of reflected pulses 3705 and diminish the peak power of the incident pulse 3704.

Figure 38:
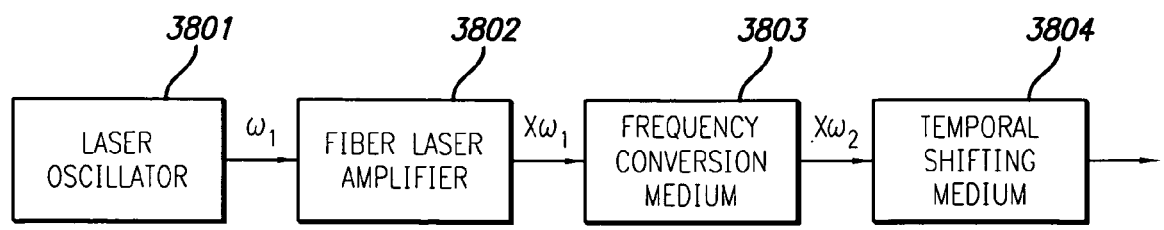
FIG. 38 shows a laser oscillator, a fiber laser amplifier, a frequency conversion medium, and a spatial smoothing medium.

To provide spatial uniformity in light brightness, the present design may further include a spatial smoothing medium. A spatial smoothing medium may improve the spatial uniformity of the brightness of the frequency-converted light. FIG. 38 shows a laser oscillator 3801, a fiber laser amplifier 3802, a frequency conversion medium 3803, and a spatial smoothing medium 3804. Various devices may serve as the spatial smoothing medium, including various combinations of diffusers, diffractive optics, lens arrays, light pipes, gratings, etalons, apertures, gradient transmission elements, apodization devices, lenses, and other optical components.

FIGS. 39A and 39B show two spatial smoothing media, including a homogenizer rod 3901 configured to receive a spatially non-uniform input and transmit a spatially uniform output, and a lens array with a focusing lens. Non-uniform illumination may strike the lens array 3902 from the left in the orientation shown. The lens array 3902 may divide the beam into many sub-beams. The focusing lens 3903 can focus all the sub-beams at an overlap plane 3904 where the illumination is spatially uniform. For simplicity, FIG. 39B shows light focusing at only two points at the overlap plane 3904, but the configuration shown may be employed to provide uniform brightness throughout the overlap plane.

FIGS. 40A, 40B, and 40C show three more examples of spatial smoothing media. In FIG. 40A, a moving piece of ground glass or a diffractive optic 4002, downstream from a focusing lens 4001, removes speckle from a laser beam. The term speckle refers to patterns of light and dark over short distance scales caused by interference. In FIG. 40B, a diffractive optic 4003 followed by a lens 4004 can provide a substantially spatially uniform brightness on the pupil plane. The spatial smoothing medium of FIG. 40C may include a diffractive optic 4006 to shape pupil illumination, a lens 4007, a diffractive optic to shape field illumination 4008, and a focusing lens 4009. Such a design may improve the spatial uniformity of frequency-converted light.

Embodiments previously presented do not employ, generate, or operate with a supercontinuum. Use and operation of an embodiment of the present design with supercontinuum aspects will now be discussed.

Figure 41:
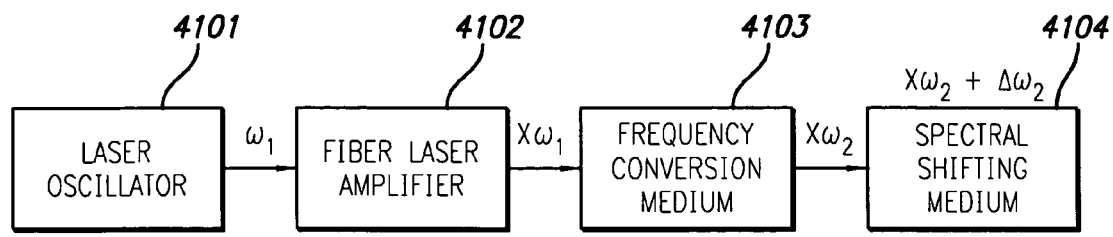
FIG. 41 illustrates laser oscillator, a fiber laser amplifier, a frequency conversion medium, and a spectral shifting medium.

Narrowband light may be transformed into broadband light. A narrowband beam of light passing through certain media may undergo Raman scattering and four-wave mixing and exit the medium as a broadband beam known as a supercontinuum. Such a medium is considered a "spectral shifting medium" due to shifting the spectrum of the incoming light. FIG. 41 illustrates laser oscillator 4101, a fiber laser amplifier 4102, a frequency conversion medium 4103, and a spectral shifting medium 4104.

Figure 42A:
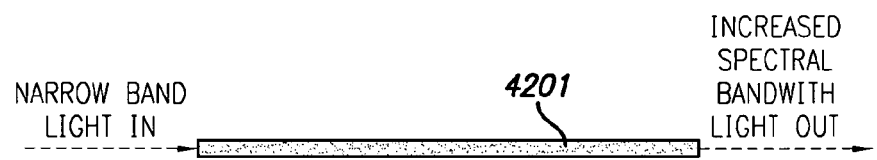
FIG. 42A represents a photonic crystal filter.
Figure 42B:
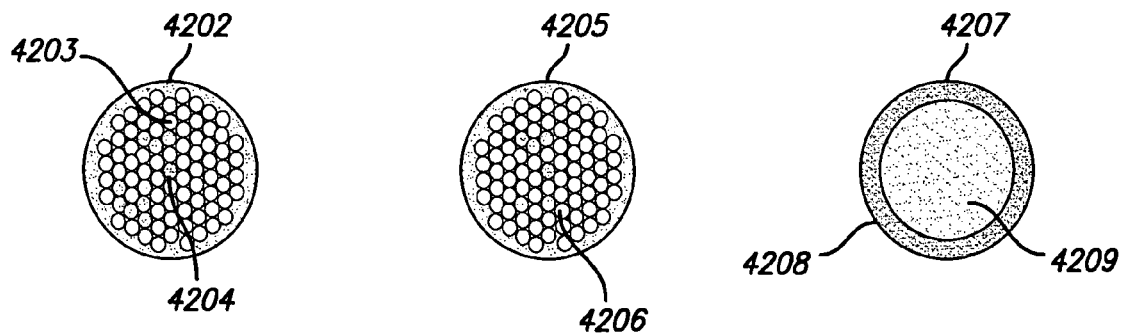
FIG. 42B shows cross sections of various spectral shifting media.
Figure 43:
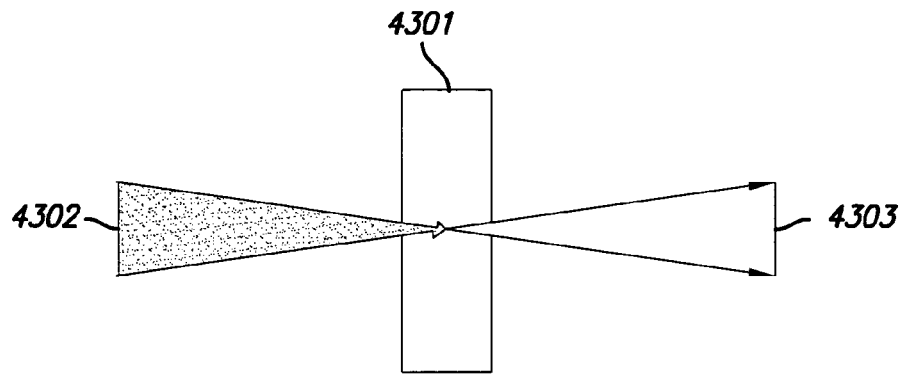
FIG. 43 illustrates a spectral shifting medium having a cell containing gas.

Different substances can serve as the spectral shifting medium. The spectral shifting medium may comprise a photonic crystal fiber, or a gas comprising one or more of the following elements: deuterium, xenon, krypton, argon, neon, helium, fluorine, and/or nitrogen. The spectral shifting medium could also be a plasma, crystal, polymer, or liquid, including but not limited to ethanol or ammonium hydroxide. FIG. 42 illustrates various spectral shifting media. A photonic crystal fiber 4201 can serve as the spectral shifting medium. A cross section of photonic crystal fiber 4202 shows air channels 4203 within the fused silica matrix 4204. A photonic crystal fiber can serve as an even more effective spectral shifting medium if the air channels are filled with gas 4206, as shown in cross-section 4205. Another spectral shifting medium is a fused silica capillary 4207, wherein gas 4209 fills the hollow core surrounded by the fused silica 4208. FIG. 43 presents another spectral shifting medium having a cell 4301 containing gas. Narrowband light 4302 enters on the left and broadband light 4303 exits on the right.

A supercontinuum may be created by pumping a laser to generate coherent light, amplifying the coherent light using one or more fiber laser amplifiers, and broadening the bandwidth of the coherent light to create a supercontinuum. Frequency converted light and non-frequency-converted light may also be broadened to create a supercontinuum, and multiple beams may be addressed. Mode locking may be employed in the single beam or multiple beam context.

Figure 44:
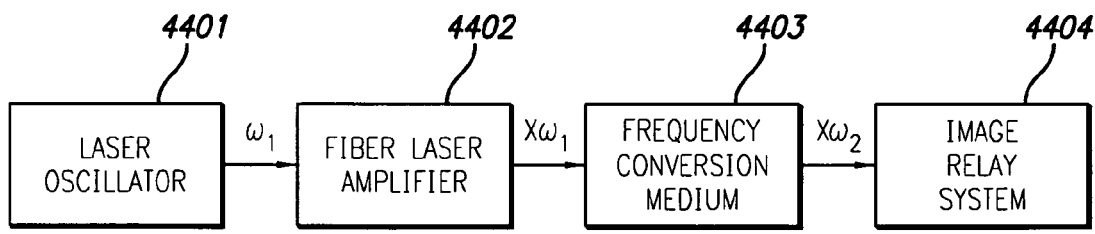
FIG. 44 shows an illumination subsystem including a laser oscillator, a fiber laser amplifier, a frequency conversion medium, and an image relay system.

The illumination subsystem of the present design may include both an illuminator and an image relay system for relaying the beam into the inspection system. As shown in FIG. 44, the illumination subsystem may include a laser oscillator 4401, a fiber laser amplifier 4402, a frequency conversion medium 4403, and an image relay system 4404.

Figure 45A:
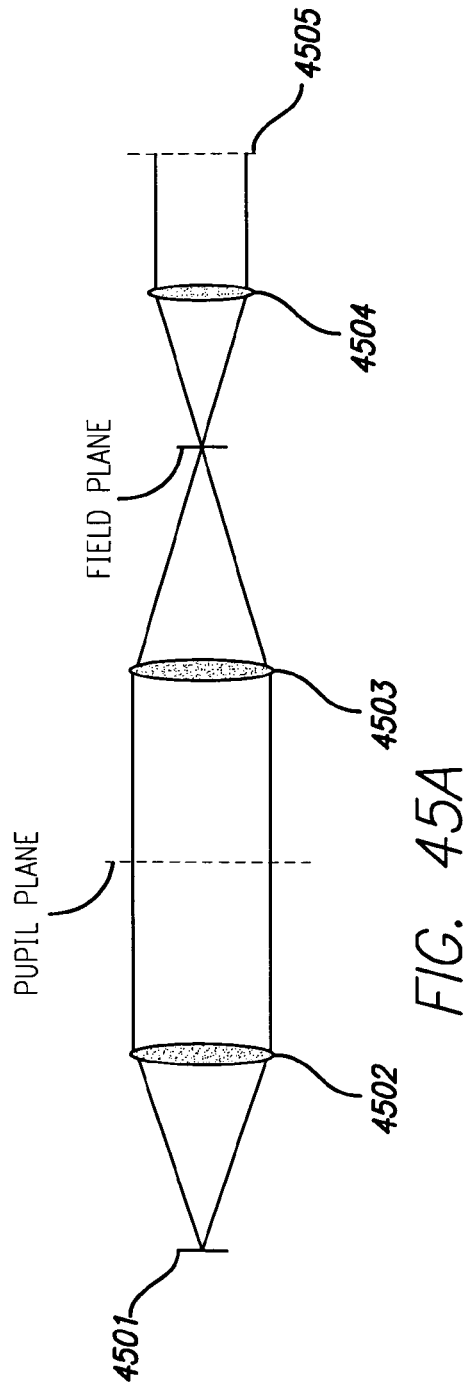
FIGS. 45A and 45B show two examples of image relay systems that may lie downstream from the configurations shown in FIGS. 39 and 40.
Figure 45B:
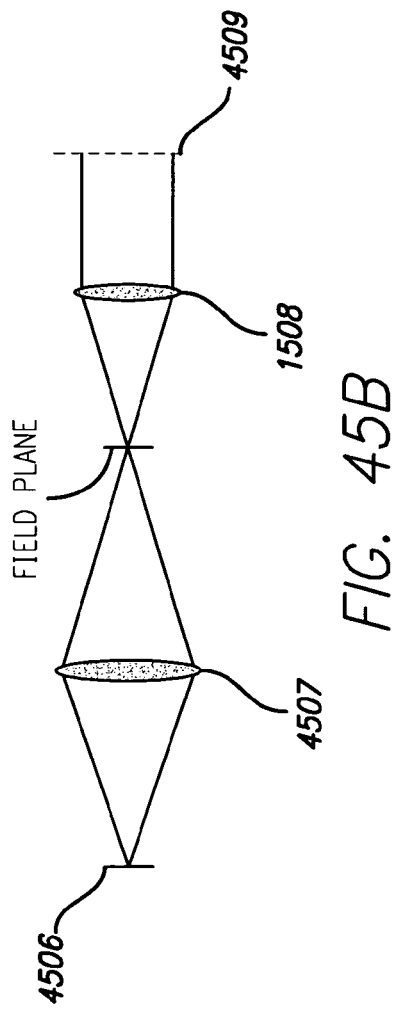

FIG. 45 shows two examples 4501 and 4506 of image relay systems that may lie downstream from the configurations shown in FIGS. 39 and 40. Both may deliver light to the pupil plane in the imaging optics 4505 and 4509. Configuration 4501 may employ three lenses 4502, 4503, and 4504, while configuration 4506 may employ two lenses 4507 and 4508. The illuminators disclosed herein may be combined with an image relay system to create an illumination subsystem.

Figure 46:
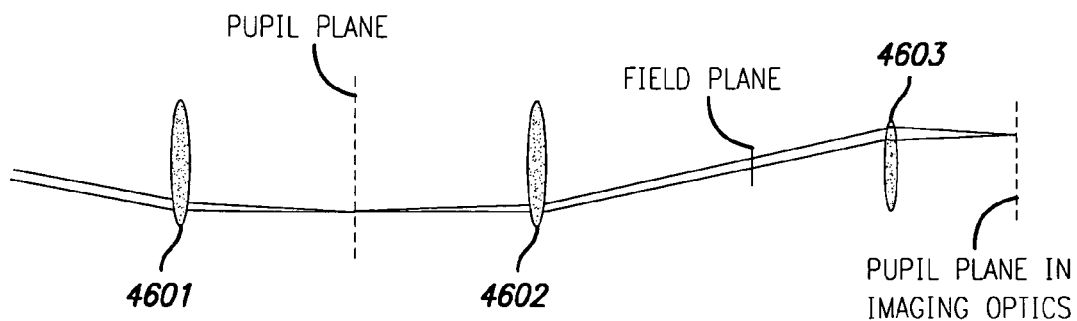
FIG. 46 is an image relay system generally designed for dark field imaging.

The image relay systems shown in FIG. 45 are generally designed for bright field imaging. The image relay system shown in FIG. 46 is generally designed for dark field imaging. The three lenses 4601, 4602, and 4603 combine to illuminate a single point in the pupil plane.

The embodiments disclosed herein may be employed in microscopes, photomask repair tools, telecommunication systems, medical diagnosis and treatment systems, and/or laboratory equipment for conducting experiments in the physical or biological sciences.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. An illuminator employed in a specimen inspection system, comprising:
    a laser arrangement comprising a laser oscillator configured to produce coherent light; and
    a plurality of parallel fiber laser amplifiers configured to receive coherent light from the laser oscillator and transmit amplified coherent light toward a specimen for purposes of inspecting the specimen;
    wherein said laser arrangement employs mode-locking to selectively produce energy bursts having desired properties.

2. The illuminator of claim 1, wherein the laser oscillator is configured to create a q-switched pulse train.

3. The illuminator of claim 1, wherein the laser oscillator is configured to create a mode-locked pulse train.

4. The illuminator of claim 1, wherein the laser oscillator comprises a device having a saturable absorber fabricated from one from a group comprising:
    a semiconducting material;
    carbon nanotubes;
    an acousto-optic modulator;
    an electro-optic modulator; and
    an electronic switch.

5. The illuminator of claim 1, each fiber laser amplifier comprising an end, wherein the end of each fiber laser amplifier is tapered.

6. The illuminator of claim 1, wherein each fiber laser amplifier comprises a photonic crystal fiber.

7. The illuminator of claim 6, wherein said photonic crystal fiber is a multi-core fiber.

8. The illuminator of claim 1, wherein each fiber laser amplifier comprises optical fiber having a modified index profile.

9. The illuminator of claim 1, wherein each fiber laser amplifier is doped with a lanthanide element comprising at least one from a group comprising ytterbium, erbium, thulium, neodymium, praseodymium, and holmium.

10. The illuminator of claim 1, wherein the plurality of fiber laser amplifiers have similar output frequencies.

11. The illuminator of claim 1, wherein the plurality of fiber laser amplifiers have different output frequencies.

12. The illuminator of claim 1, wherein the laser oscillator comprises a fiber laser oscillator.

13. The illuminator of claim 1, wherein the laser arrangement comprises a plurality of laser oscillators having similar emission wavelengths.

14. The illuminator of claim 1, further comprising at least one frequency conversion medium.

15. A method for inspecting a specimen, comprising:
    pumping a laser oscillator within a laser arrangement to generate coherent light;
    amplifying said coherent light using a fiber laser amplifier; and
    transmitting amplified coherent light from the fiber laser amplifier toward the specimen for purposes of inspecting the specimen;
    wherein said laser arrangement employs mode-locking to selectively produce energy bursts having desired properties and wherein said amplifying and transmitting occurs free of supercontinuum processing.

16. The method of claim 15, further comprising:
    controlling light polarization in the fiber laser amplifier substantially simultaneous with the amplifying.

17. The method of claim 15, further comprising:
    mode-locking each laser after the pumping to create at least one pulsed output beam.

18. The method of claim 15, further comprising:
    q-switching each laser after the pumping to create at least one pulsed output beam.

19. The method of claim 15, further comprising:
    mode-locking each laser after the pumping to create at least one pulsed output beam.

20. The method of claim 15, further comprising:
    q-switching each laser after the pumping to create at least one pulsed output beam.

21. The method of claim 15, further comprising: converting coherent light frequency for a portion of said coherent light.

22. An illuminator employed in a specimen inspection system, comprising:
    a laser arrangement comprising a laser oscillator configured to be pumped to generate coherent light; and
    a fiber laser amplifier arrangement comprising a plurality of fiber laser amplifiers connected in parallel and configured to amplify coherent light generated by the at least one laser oscillator and transmit amplified coherent light toward a specimen for purposes of inspecting the specimen;
    wherein said laser oscillator employs mode-locking to selectively produce energy bursts having desired properties.

23. The illuminator of claim 22, wherein the fiber laser amplifier arrangement comprises a photonic crystal fiber.

24. The illuminator of claim 23, wherein said photonic crystal fiber is a multi-core fiber.

25. The illuminator of claim 22, wherein the plurality of fiber laser amplifiers have similar output frequencies.

26. The illuminator of claim 22, wherein the plurality of fiber laser amplifiers have different output frequencies.

27. The illuminator of claim 22, wherein the coherent light has a bandwidth, the illuminator further comprising:
    means for broadening the bandwidth of said coherent light to create a supercontinuum.

* * * * *